US012337064B2

(12) United States Patent

Edwards et al.

(10) Patent No.: US 12,337,064 B2
(45) Date of Patent: Jun. 24, 2025

(54) FORMULATIONS AND COMPOSITIONS FOR ORTHO- AND/OR RETRO-NASAL DELIVERY AND ASSOCIATED SYSTEMS, METHODS AND ARTICLES

(71) Applicant: SENSORY CLOUD, LLC, Boston, MA (US)

(72) Inventors: David A. Edwards, Cambridge, MA (US); Tom Devlin, Somerville, MA (US)

(73) Assignee: SENSORY CLOUD, INC., Boston, MA (US)

(*) Notice: Subject to any disclaimer, the term of this patent is extended or adjusted under 35 U.S.C. 154(b) by 155 days.

(21) Appl. No.: 17/273,689

(22) PCT Filed: Sep. 4, 2019

(86) PCT No.: PCT/US2019/049541

§ 371 (c)(1),
(2) Date: Mar. 4, 2021

(87) PCT Pub. No.: WO2020/096686

PCT Pub. Date: May 14, 2020

(65) Prior Publication Data

US 2021/0315811 A1 Oct. 14, 2021

Related U.S. Application Data

(60) Provisional application No. 62/727,123, filed on Sep. 5, 2018.

(51) Int. Cl.
*A61K 9/00* (2006.01)
*A23L 33/105* (2016.01)
(Continued)

(52) U.S. Cl.
CPC .......... *A61K 9/0078* (2013.01); *A23L 33/105* (2016.08); *A61K 31/045* (2013.01); *A61K 31/202* (2013.01); *A61K 31/465* (2013.01); *A61K 35/00* (2013.01); *A61K 36/185* (2013.01); *A61K 36/22* (2013.01); *A61K 36/42* (2013.01); *A61K 36/54* (2013.01); *A61K 36/73* (2013.01); *A61K 36/752* (2013.01); *A61K 36/81* (2013.01);
(Continued)

(58) Field of Classification Search
CPC .. A61K 9/0078; A61K 31/045; A61K 31/202; A61K 31/465; A61K 35/00; A61K 36/185; A61K 36/22; A61K 36/42; A61K 36/54; A61K 36/73; A61K 36/752; A61K 36/81; A61K 36/8962; A61K 36/899; A61K 36/9068; A61K 45/06; A61K 9/0095; A61K 9/0043; A61K 33/00; A61K 36/53; A61K 31/4525; A61K 33/18; A61K 33/14; A23L 33/105; A23L 33/10; A61M 11/003; A61M 15/0003; A61M 15/009; A61M 15/08; A61M 2205/0294; A61M 2205/50; A61M 15/0028; A61M 2202/0468; A61M 2202/064; A61M 2205/103; A61M 2205/106; A61M 2205/14; A61M 2205/215; A61M 2205/3306; A61M 2205/3317; A61M 2205/332; A61M 2205/3592; A61M 2205/584; A61M 2205/587; A61M 2205/8206; A61M 2205/8268; A61M 2205/8293; A61M 2209/01; A61M 2209/045; A61M 2209/086; A61M 2210/065; A61M 11/005; A61M 15/0085; A23V 2002/00; A61J 1/062; A61J 1/065; A61J 1/1487; A61P 3/02; A61P 25/36; G16H 20/13
See application file for complete search history.

(56) References Cited

U.S. PATENT DOCUMENTS

| | | | |
|---|---|---|---|
| D79,717 | S | 10/1929 | Hoffman |
| D99,764 | S | 5/1936 | Trompeter |

(Continued)

FOREIGN PATENT DOCUMENTS

| | | | |
|---|---|---|---|
| CN | 1642583 | A | 7/2005 |
| CN | 1696930 | A | 11/2005 |

(Continued)

OTHER PUBLICATIONS

Chinese Office Action dated Apr. 19, 2017 for Chinese Application No. 201480025108.4 in 8 pages.

(Continued)

*Primary Examiner* — Aaron J Kosar
*Assistant Examiner* — Jennifer Lynn Cain
(74) *Attorney, Agent, or Firm* — Cozen O'Connor

(57) ABSTRACT

A composition of food or therapeutic and other substances for administration as a cloud of droplets, the cloud comprising readily-soluble droplets having a median size range of approximately 3 microns to approximately 20 microns, or 5 microns to 10 microns, or 6 microns to 10 microns, for introduction to an animal via an ortho-nasal or retro-nasal route. Agonists or antagonists may include one or more of the following: sodium iodide, sodium chloride, magnesium chloride, capsaicin, piperine, linalool, ground cinnamon, a cannabinoid, pimento, onion, clove, thyme, ginger, menthol, or TRPV antagonists, and chocolate, Irish cream, caramel, lemon, lime, mango, raspberry, watermelon, blueberry, strawberry, mint, popcorn, meat, Resolvin D2 or nicotine. Devices for delivering compositions as an aerosol are described.

12 Claims, 13 Drawing Sheets

(51) Int. Cl.

| | |
|---|---|
| ***A61K 31/045*** | (2006.01) |
| ***A61K 31/202*** | (2006.01) |
| ***A61K 31/465*** | (2006.01) |
| ***A61K 35/00*** | (2006.01) |
| ***A61K 36/185*** | (2006.01) |
| ***A61K 36/22*** | (2006.01) |
| ***A61K 36/42*** | (2006.01) |
| ***A61K 36/54*** | (2006.01) |
| ***A61K 36/73*** | (2006.01) |
| ***A61K 36/752*** | (2006.01) |
| ***A61K 36/81*** | (2006.01) |
| ***A61K 36/8962*** | (2006.01) |
| ***A61K 36/899*** | (2006.01) |
| ***A61K 36/9068*** | (2006.01) |
| ***A61K 45/06*** | (2006.01) |
| ***A61M 11/00*** | (2006.01) |
| ***A61M 15/00*** | (2006.01) |
| ***A61M 15/08*** | (2006.01) |

(52) U.S. Cl.

CPC ........ *A61K 36/8962* (2013.01); *A61K 36/899* (2013.01); *A61K 36/9068* (2013.01); *A61K 45/06* (2013.01); *A61M 11/003* (2014.02); *A61M 15/0003* (2014.02); *A61M 15/009* (2013.01); *A61M 15/08* (2013.01); *A23V 2002/00* (2013.01); *A61M 2205/0294* (2013.01); *A61M 2205/50* (2013.01)

(56) References Cited

U.S. PATENT DOCUMENTS

| | | | |
|---|---|---|---|
| D163,210 | S | 5/1951 | Long |
| D172,852 | S | 8/1954 | Koert |
| 2,844,469 | A | 7/1958 | Daniel et al. |
| 3,163,544 | A | 12/1964 | Valyi |
| D211,154 | S | 5/1968 | Pizzurro |
| D211,505 | S | 6/1968 | Anderson |
| D213,331 | S | 2/1969 | Yutzey |
| 3,669,313 | A | 6/1972 | Marand et al. |
| D224,882 | S | 10/1972 | Alpern |
| 3,781,164 | A | 12/1973 | McCaffery |
| D247,533 | S | 3/1978 | Noyes |
| 4,258,874 | A | 3/1981 | Webinger et al. |
| D281,281 | S | 11/1985 | Matalon |
| 4,556,539 | A | 12/1985 | Spector |
| 4,583,686 | A | 4/1986 | Martens et al. |
| D288,713 | S | 3/1987 | Darneal |
| 4,790,479 | A | 12/1988 | Matsumoto et al. |
| D306,235 | S | 2/1990 | Tamamura |
| 4,968,456 | A | 11/1990 | Muderlak et al. |
| D315,789 | S | 3/1991 | Muderlak |
| D321,284 | S | 11/1991 | Marsella et al. |
| D326,223 | S | 5/1992 | Dova |
| D327,037 | S | 6/1992 | Martineau |
| D328,025 | S | 7/1992 | Farricielli |
| 5,170,782 | A | 12/1992 | Kocinski |
| 5,178,327 | A | 1/1993 | Palamand et al. |
| 5,195,633 | A | 3/1993 | Kaminski |
| 5,273,690 | A | 12/1993 | McDowell |
| D349,335 | S | 8/1994 | Wang |
| D363,509 | S | 10/1995 | Parekh et al. |
| D381,515 | S | 7/1997 | Haynes |
| D389,411 | S | 1/1998 | Baron |
| 5,724,256 | A | 3/1998 | Lee et al. |
| 5,805,768 | A | 9/1998 | Schwartz et al. |
| 5,897,325 | A | 4/1999 | Koby-Olson |
| 5,908,158 | A | 6/1999 | Cheiman |
| D411,881 | S | 7/1999 | Weick |
| 5,967,045 | A | 10/1999 | Staiger et al. |
| D431,902 | S | 10/2000 | Mellin |
| 6,152,383 | A | 11/2000 | Chen |
| D438,608 | S | 3/2001 | Chen |
| D446,849 | S | 8/2001 | Weinberg |
| D468,626 | S | 1/2003 | Joedal et al. |
| 6,581,915 | B2 | 6/2003 | Bartsch et al. |
| D477,390 | S | 7/2003 | Chen |
| 6,654,664 | B1 | 11/2003 | Chiao |
| D496,451 | S | 9/2004 | Julos et al. |
| D496,585 | S | 9/2004 | McBride et al. |
| 6,803,987 | B2 | 10/2004 | Manne |
| D512,494 | S | 12/2005 | Haranaka |
| D513,070 | S | 12/2005 | Haranaka |
| D519,624 | S | 4/2006 | Chen |
| D525,488 | S | 7/2006 | McWhorter |
| D525,871 | S | 8/2006 | Zeh et al. |
| D527,182 | S | 8/2006 | Ham |
| D532,695 | S | 11/2006 | Grant |
| 7,201,167 | B2 | 4/2007 | Fink et al. |
| D546,688 | S | 7/2007 | Verburg |
| D548,317 | S | 8/2007 | Newton et al. |
| D548,969 | S | 8/2007 | Bramley |
| D559,434 | S | 1/2008 | Morris et al. |
| D560,018 | S | 1/2008 | Morris et al. |
| D560,788 | S | 1/2008 | Farrell et al. |
| D565,956 | S | 4/2008 | Fougere et al. |
| D574,072 | S | 7/2008 | Carlson et al. |
| 7,400,822 | B2 | 7/2008 | Ruiz et al. |
| D575,384 | S | 8/2008 | Huang |
| D575,859 | S | 8/2008 | Scimone |
| D575,860 | S | 8/2008 | Wu |
| D577,547 | S | 9/2008 | Willat et al. |
| D582,063 | S | 12/2008 | Spangler et al. |
| D582,534 | S | 12/2008 | Conway et al. |
| D583,450 | S | 12/2008 | Choi |
| D583,451 | S | 12/2008 | Aloe et al. |
| D583,452 | S | 12/2008 | Aloe et al. |
| D593,669 | S | 6/2009 | Daelemans et al. |
| D597,192 | S | 7/2009 | Drucker et al. |
| D601,343 | S | 10/2009 | Franczyk et al. |
| 7,610,118 | B2 | 10/2009 | Schramm et al. |
| D604,099 | S | 11/2009 | Mishan |
| D611,584 | S | 3/2010 | Gruenbacher et al. |
| D611,585 | S | 3/2010 | Gruenbacher et al. |
| D613,844 | S | 4/2010 | Joergensen |
| D620,365 | S | 7/2010 | Desjardins |
| D620,742 | S | 8/2010 | Lion et al. |
| D625,398 | S | 10/2010 | Choi |
| 7,824,627 | B2 | 11/2010 | Michaels et al. |
| D632,771 | S | 2/2011 | Abbondanzio et al. |
| D633,190 | S | 2/2011 | Abbondanzio et al. |
| D633,610 | S | 3/2011 | Wu |
| D634,538 | S | 3/2011 | Dumas |
| D637,274 | S | 5/2011 | Chan et al. |
| 7,963,460 | B2 | 6/2011 | Joergensen |
| 7,976,782 | B2 | 7/2011 | Matsuura et al. |
| D643,103 | S | 8/2011 | Bilko et al. |
| 7,992,801 | B2 | 8/2011 | Joergensen |
| 8,001,962 | B2 | 8/2011 | Sheiman |
| 8,001,963 | B2 | 8/2011 | Giroux |
| D644,725 | S | 9/2011 | Kim |
| D646,926 | S | 10/2011 | Willat et al. |
| D647,187 | S | 10/2011 | Chan et al. |
| D647,193 | S | 10/2011 | Kim |
| 8,032,014 | B2 | 10/2011 | Cheung |
| D651,090 | S | 12/2011 | Grima et al. |
| D654,761 | S | 2/2012 | Herbst |
| D656,230 | S | 3/2012 | Robinson et al. |
| D662,201 | S | 6/2012 | Edwards et al. |
| D662,578 | S | 6/2012 | Blanking et al. |
| D662,579 | S | 6/2012 | Blanking et al. |
| D662,580 | S | 6/2012 | Blanking et al. |
| D664,446 | S | 7/2012 | Edwards |
| D672,860 | S | 12/2012 | Blachford et al. |
| 8,336,545 | B2 | 12/2012 | Fink et al. |
| D675,304 | S | 1/2013 | Valentino et al. |
| D675,309 | S | 1/2013 | Freeborn et al. |
| D675,434 | S | 2/2013 | Vernall et al. |
| D676,239 | S | 2/2013 | Benoit et al. |
| 8,385,730 | B2 | 2/2013 | Bushman et al. |
| D680,637 | S | 4/2013 | Blachford et al. |
| D681,182 | S | 4/2013 | Tomas et al. |

(56) References Cited

U.S. PATENT DOCUMENTS

| | | | |
|---|---|---|---|
| D681,183 | S | 4/2013 | Blachford et al. |
| D685,608 | S | 7/2013 | Bangert |
| D686,817 | S | 7/2013 | Dennis |
| 8,485,454 | B1 | 7/2013 | Irvin et al. |
| D689,999 | S | 9/2013 | Viala |
| D696,892 | S | 1/2014 | Bretillot |
| 8,627,821 | B2 | 1/2014 | Edwards et al. |
| D705,918 | S | 5/2014 | Robinson et al. |
| 8,758,824 | B2 | 6/2014 | Lipp et al. |
| D715,051 | S | 10/2014 | Tung et al. |
| D716,432 | S | 10/2014 | Mala et al. |
| D716,433 | S | 10/2014 | Milon et al. |
| D720,526 | S | 1/2015 | Lopez-Stout |
| 8,992,983 | B2 | 3/2015 | Lipp et al. |
| D729,369 | S | 5/2015 | Viala et al. |
| 9,061,352 | B2 | 6/2015 | Lipp et al. |
| 9,119,778 | B2 | 9/2015 | Sung et al. |
| 9,233,158 | B2 | 1/2016 | Lipp et al. |
| 9,238,005 | B2 | 1/2016 | Sung et al. |
| 9,573,154 | B2 | 2/2017 | Bretillot et al. |
| 9,642,798 | B2 | 5/2017 | Lipp et al. |
| 9,737,518 | B2 | 8/2017 | Sung et al. |
| 9,744,130 | B2 | 8/2017 | Lipp et al. |
| 9,931,425 | B2 | 4/2018 | Edwards et al. |
| 10,376,465 | B2 | 8/2019 | Lipp et al. |
| 10,589,039 | B2 | 3/2020 | Dehaan et al. |
| 10,806,871 | B2 | 10/2020 | Dehaan et al. |
| 2002/0054856 | A1 | 5/2002 | Jones |
| 2002/0066798 | A1 | 6/2002 | Laudamiel-Pellet et al. |
| 2002/0068009 | A1 | 6/2002 | Laudamiel-Pellet et al. |
| 2002/0068010 | A1 | 6/2002 | Laudamiel-Pellet et al. |
| 2002/0069465 | A1 | 6/2002 | Chute et al. |
| 2003/0020185 | A1 | 1/2003 | Cox |
| 2003/0175148 | A1 | 9/2003 | Kvietok et al. |
| 2003/0195816 | A1 | 10/2003 | Dziaba et al. |
| 2003/0206834 | A1 | 11/2003 | Chiao et al. |
| 2004/0040557 | A1 | 3/2004 | Salter et al. |
| 2005/0062841 | A1 | 3/2005 | Rivera-Cintron |
| 2005/0160789 | A1 | 7/2005 | Freyer et al. |
| 2005/0163649 | A1 | 7/2005 | Friedrich et al. |
| 2005/0195367 | A1 | 9/2005 | Selander et al. |
| 2005/0227745 | A1 | 10/2005 | Chiang et al. |
| 2005/0229926 | A1 | 10/2005 | Fink et al. |
| 2005/0265904 | A1 | 12/2005 | Hardy et al. |
| 2005/0278224 | A1 | 12/2005 | Bannai et al. |
| 2006/0037970 | A1 | 2/2006 | Fazzio et al. |
| 2006/0039835 | A1 | 2/2006 | Nottingham et al. |
| 2006/0137680 | A1 | 6/2006 | Sheiman |
| 2006/0155225 | A1 | 7/2006 | Murdock et al. |
| 2006/0196100 | A1 | 9/2006 | Laudamiel-Pellet et al. |
| 2006/0249518 | A1 | 11/2006 | Festa |
| 2007/0027696 | A1 | 2/2007 | Burger |
| 2007/0041865 | A1 | 2/2007 | Ayoub et al. |
| 2007/0050083 | A1 | 3/2007 | Signorelli et al. |
| 2007/0053844 | A1 | 3/2007 | Watanabe et al. |
| 2007/0067104 | A1 | 3/2007 | Mays |
| 2007/0076403 | A1 | 4/2007 | McGrew |
| 2007/0204511 | A1 | 9/2007 | Lee et al. |
| 2007/0243791 | A1 | 10/2007 | Stedman |
| 2007/0258849 | A1 | 11/2007 | Kent |
| 2007/0262477 | A1 | 11/2007 | Brown et al. |
| 2007/0267010 | A1 | 11/2007 | Fink et al. |
| 2007/0270502 | A1 | 11/2007 | Edwards et al. |
| 2008/0093474 | A1 | 4/2008 | Suissa et al. |
| 2008/0187609 | A1 | 8/2008 | Vail et al. |
| 2008/0230053 | A1 | 9/2008 | Kraft et al. |
| 2008/0245362 | A1 | 10/2008 | Moessis et al. |
| 2008/0279731 | A1 | 11/2008 | Goreham et al. |
| 2008/0292508 | A1 | 11/2008 | Zlotnik et al. |
| 2008/0299049 | A1 | 12/2008 | Stangl |
| 2009/0196930 | A1 | 8/2009 | Surber et al. |
| 2009/0200399 | A1 | 8/2009 | Mcgee et al. |
| 2010/0096409 | A1 | 4/2010 | Wainwright |
| 2010/0114819 | A1 | 5/2010 | Kim et al. |
| 2010/0193542 | A1 | 8/2010 | Macler |
| 2010/0243754 | A1 | 9/2010 | Harris |
| 2010/0309434 | A1 | 12/2010 | Van et al. |
| 2011/0011394 | A1 | 1/2011 | Edwards et al. |
| 2011/0024521 | A1 | 2/2011 | Joergensen |
| 2011/0049266 | A1 | 3/2011 | Joergensen |
| 2011/0079660 | A1 | 4/2011 | Joergensen |
| 2011/0186047 | A1 | 8/2011 | Lewis et al. |
| 2011/0226864 | A1 | 9/2011 | Kim et al. |
| 2011/0247718 | A1 | 10/2011 | Samain |
| 2011/0280767 | A1 | 11/2011 | Goessens |
| 2012/0022114 | A1 | 1/2012 | Cassara et al. |
| 2013/0173315 | A1 | 7/2013 | Dorsey |
| 2013/0281361 | A1 | 10/2013 | Hava et al. |
| 2013/0292414 | A1 | 11/2013 | Sutherland |
| 2013/0304255 | A1 | 11/2013 | Ratnakar |
| 2013/0334337 | A1 | 12/2013 | Haran et al. |
| 2014/0001286 | A1 | 1/2014 | Scott et al. |
| 2014/0081777 | A1 | 3/2014 | Mastrodonato et al. |
| 2014/0134251 | A1 | 5/2014 | Lipp et al. |
| 2014/0216603 | A1 | 8/2014 | Brown |
| 2014/0230313 | A1 | 8/2014 | Elman |
| 2014/0336159 | A1 | 11/2014 | Clarke et al. |
| 2014/0377130 | A1 | 12/2014 | Edwards et al. |
| 2015/0048178 | A1 | 2/2015 | Edwards et al. |
| 2015/0079173 | A1 | 3/2015 | Edwards et al. |
| 2015/0231066 | A1 | 8/2015 | Lipp et al. |
| 2015/0250875 | A1 | 9/2015 | Lipp et al. |
| 2017/0070845 | A1 | 3/2017 | Edwards et al. |
| 2017/0076403 | A1 | 3/2017 | Edwards et al. |
| 2017/0151362 | A1 | 6/2017 | Edwards et al. |
| 2017/0232130 | A1 | 8/2017 | Conroy et al. |
| 2017/0239428 | A1 | 8/2017 | Banoun |
| 2018/0036449 | A1 | 2/2018 | Edwards et al. |
| 2019/0105460 | A1 | 4/2019 | Edwards et al. |
| 2019/0388342 | A1 | 12/2019 | Sung et al. |

FOREIGN PATENT DOCUMENTS

| | | | | |
|---|---|---|---|---|
| CN | 100461154 | C | 2/2009 | |
| DE | 10065545 | A1 | 7/2002 | |
| EP | 0332260 | A2 | 9/1989 | |
| EP | 0831384 | A1 | 3/1998 | |
| EP | 1098195 | A2 | 5/2001 | |
| EP | 1066850 | B1 | 8/2006 | |
| EP | 2771052 | A2 | 9/2014 | |
| GB | 2469876 | A | 11/2010 | |
| JP | H05277188 | A | 10/1993 | |
| JP | H11504567 | A | 4/1999 | |
| JP | 2003123036 | A | 4/2003 | |
| JP | 2003162212 | A | 6/2003 | |
| JP | 2005538822 | A | 12/2005 | |
| JP | 2006048611 | A | 2/2006 | |
| JP | 2008211605 | A | 9/2008 | |
| JP | 2009265453 | A | 11/2009 | |
| JP | 2011224071 | A | 11/2011 | |
| JP | 2012198694 | A | 10/2012 | |
| KR | 20080046870 | A | 5/2008 | |
| KR | 100927636 | B1 | 11/2009 | |
| KR | 20160145396 | A | 12/2016 | |
| WO | 9731721 | A1 | 9/1997 | |
| WO | 9901793 | A1 | 1/1999 | |
| WO | 0053301 | A1 | 9/2000 | |
| WO | 0209772 | A2 | 2/2002 | |
| WO | 0209773 | A2 | 2/2002 | |
| WO | 0209776 | A2 | 2/2002 | |
| WO | 03077962 | A2 | 9/2003 | |
| WO | 03088627 | A2 | 10/2003 | |
| WO | 03098971 | A1 | 11/2003 | |
| WO | 2004017848 | A1 | 3/2004 | |
| WO | 2006074562 | A1 | 7/2006 | |
| WO | WO-2006122156 | A2 * | 11/2006 | ........... A61K 31/427 |
| WO | 2007073505 | A2 | 6/2007 | |
| WO | 2007117675 | A2 | 10/2007 | |
| WO | 2008042951 | A2 | 4/2008 | |
| WO | 2009000043 | A1 | 12/2008 | |
| WO | 2009062518 | A1 | 5/2009 | |
| WO | 2009086470 | A2 | 7/2009 | |
| WO | 2009101571 | A1 | 8/2009 | |
| WO | 2010008172 | A2 | 1/2010 | |

(56) References Cited

FOREIGN PATENT DOCUMENTS

| | | |
|---|---|---|
| WO | 2010065744 A2 | 6/2010 |
| WO | 2010105991 A1 | 9/2010 |
| WO | 2011028259 A2 | 3/2011 |
| WO | 2012038477 A1 | 3/2012 |
| WO | 2012101642 A2 | 8/2012 |
| WO | 2013006809 A2 | 1/2013 |
| WO | 2013063119 A2 | 5/2013 |
| WO | 2014089506 A1 | 6/2014 |
| WO | 2014144636 A2 | 9/2014 |
| WO | 2014144690 A2 | 9/2014 |
| WO | 2014151329 A1 | 9/2014 |
| WO | 2015054280 A1 | 4/2015 |

OTHER PUBLICATIONS

Chinese Office Action dated Mar. 2, 2017 for Chinese Application No. 201480022939.6 in 4 pages.
Communication pursuant to Article 94(3) in related European Application No. 12 791 597.3-1113 dated Mar. 18, 2019, in 6 pages.
Extended European Search Report, dated Aug. 3, 2017, for European Application No. 14853938.0-1370 / 3077014, 8 pages.
Extended European Search Report, dated Sep. 6, 2017, for European Application No. 14883745.3-1871, 8 pages.
International Preliminary Report on Patentability and Written Opinion from PCT Application No. PCT/US2012/061695 dated Apr. 29, 2014.
International Preliminary Report on Patentability with Written Opinion issued Sep. 15, 2015 for International Application No. PCT/US2014/029132, 12 pages.
International Preliminary Report on Patentability with Written Opinion issued Sep. 15, 2015 for International Application No. PCT/US2014/029208, 11 pages.
International Preliminary Report on Patentability, dated Aug. 30, 2016, for International Application No. PCT/US2014/060643, 8 pages.
International Search Report and Written Opinion for PCT/US2018/050250 dated Mar. 11, 2019 in 15 pages.
International Search Report and Written Opinion for PCT/US2019/049541, mailed Jun. 5, 2020, 12 pages.
International Search Report and Written Opinion for PCT/US2020/027691 dated Jul. 29, 2020, 15 pages.
International Search Report and Written Opinion issued Jul. 30, 2020 in PCT/US2020/027818, 16 pages.
International Search Report and Written Opinion, mailed Jan. 11, 2017, for International Application No. PCT/US2016/055541, 10 pages.
International Search Report and Written Opinion, mailed Jun. 2, 2016, for International Application No. PCT/US2016/017781, 13 pages.
International Search Report and Written Opinion, mailed Nov. 8, 2016, for International Application No. PCT/US2016/044553, 11 pages.
International Search Report from PCT Application No. PCT/US2012/061695 dated May 22, 2013, in 7 pages.
International Search Report mailed Dec. 17, 2014, for International Application No. PCT/US2014/029132, 5 bages.
International Search Report mailed Feb. 3, 2015, for International Application No. PCT/US2014/060643, 3 pages.
International Search Report mailed Feb. 9, 2015, for International Application No. PCT/US2014/029208, 5 pages.
International Search Report mailed Jan. 12, 2015, for International Application No. PCT/US2014/060614, 3 pages.
International Search Report mailed Jan. 16, 2015, for International Application No. PCT/US2014/060630, 3 pages.
International Search Report mailed Sep. 21, 2015, for International Application No. PCT/US2015/035805, 3 pages.
Japanese Office Action, mailed Mar. 6, 2018, for Japanese Application No. 2016-503015, 14 pages. (with English Translation).
Maslin, Polyester, An Offbeat Comedy. New York Times, May 29, 1981.
McGean-Rohco Inc., "Honey BeeTM Aerogel Air Freshener," Data Sheet, 2004, 2 pages.
Polyester Oderama Technology. Scent Card. 1981.
Written Opinion mailed Dec. 17, 2014, for International Application No. PCT/US2014/029132, 11 pages.
Written Opinion mailed Feb. 3, 2015, for International Application No. PCT/US2014/060643, 7 pages.
Written Opinion mailed Feb. 9, 2015, for International Application No. PCT/US2014/029208, 11 pages.
Written Opinion mailed Jan. 12, 2015, for International Application No. PCT/US2014/060614, 10 pages.
Written Opinion mailed Jan. 16, 2015, for International Application No. PCT/US2014/060630, 17 pages.
Written Opinion mailed May 22, 2013, for International Application No. PCT/US2012/061695, 10 pages.
Written Opinion mailed Sep. 21, 2015, for International Application No. PCT/US2015/035805, 8 pages.
Boehret, Katherine , "Does your air freshener need an app?" The Verge, Apr. 27, 2016, retrieved from URL=https://www.theverge.com/2016/4/27/11514206/your-air-freshener-just-got-a-lot-smarter, downloaded on Jun. 11, 2019.
Grobman, M. E. , et al., "The TRPV1 receptor agonist capsaicin is an ineffective bronchoprovocant in an experimental model of feline asthma".
Ryan, William R, et al., "Safety of a preservative-free acidified saline nasal spray: a randomized, double-blind, placebo-controlled, crossover clinical trial", Randomized Controlled Trial; Arch Otolaryngol Head Neck Surg. Nov. 2010; 136(11):1099-103.
Smutzer, Gregory , et al., "Integrating TRPV1 Receptor Function with Capsaicin Psychophysics".
Van Geffen, et al., "Comparative in-vitro Study of the Trachospray a New Device for Topical Anesthesia of the Upper Airway", Medical Devices: Evidence and Research 2021:14, DovePress, 8 pages.
Vangeffen, et al., "Clinical Evaluation of the trachospray device for upper airway anaesthesia", Anesthesia 2020, Science Letter, 2 pages.
Aero Pump Medspray "Innovative Spray Nozzle From Medspray", Brochure, 4 pages.
Armstrong, et al., "Calcium block of Na + channels and its effect on closing rate", Proc. Natl. Acad. Sci. USA, vol. 96, pp. 4154-4157, Mar. 1999 Physiology.
Blom H. M. et al: "Intranasal capsaicin is efficacious in non-allergic, non-infectious perennial rhinitis. A placebo-controlled study". Clinical & Experimental Allergy, vol. 27, No. 7, Jul. 1, 1997 (Jul. 1, 1997), pp. 796-801, XP055932787.
Casini, et al., "Intracellular calcium modulation of voltage-gated sodium channels in ventricular myocytes", Cardiovascular Research (2009) 81, 72-81.
Catterall, et al., "Structural Basis for Pharmacology of Voltage-Gated Sodium and Calcium Channels", Molecular Pharmacology Mol Pharmacol 88:141-150, Jul. 2015, The American Society for Pharmacology and Experimental Therapeutics.
De Baaij, et al., "Regulation of magnesium balance: lessons learned from human genetic disease", Clin Kidney J (2012) 5 [Suppl 1]: i15-i24doi: 10.1093/ndtplus/sfr164. 10 pages.
Ferretti, et al., "Expression of calcium-buffering proteins in rat intrinsic laryngeal muscles", Physiol Rep, vol. 3, Iss. 6), 2015, e12409, 10 pages.
Gourgoulianis, et al., Magnesium as a Relaxing Factor of Airway Smooth Muscles, Journal of Aerosol Medicine, vol. 14, No. 3 ,2001 Mary Ann Liebert, Inc., pp. 301-307.
Gu, et al., "Effects of [Ca2+]i and pH on epithelial Na+ channel activity of cultured mouse cortical collecting ducts"; Journal of Experimental Bio. 211, pp. 3167-3173.
Haidl, et al., "Inhaled isotonic alkaline versus saline solution and radioaerosol clearance in chronic cough", ERS Journals Ltd 2000, European, 7 pages.

(56) References Cited

OTHER PUBLICATIONS

Hansen Eva et al: "A Comparison of Oral Sensory Effects of Three TRPA 1 Agonists in Young Adult Smokers and Non-smokers", Frontiers in Physiology, vol. 8, Sep. 7, 2017 (Sep. 7, 2017), XP055933070.
Hoffmann, et al., "Physiology of Cell vol. Regulation in Vertebrates", Physiol Rev 89: 193-277, 2009; dio:10.1152/physrev.00037.2007.
Hudson RCI, "Product Catalog 2004-2005", 91 pages.
Hudson Respiratory Care, Oxygen Therapy, Aerosol Therapy, Incentive Spirometers, Teleflex, Nov. 2011, 24 pages.
Medspray, "Ultra-soft Nasal Sprays", Brochure, Journal of Aerosol Medicine and Pulmonary Drug Delivery, Aug. 29, 2019, 2 pages.
Medspray-Aptar Pharmas PureHale , "Our Products", Brochure 2020 Medspray, 13 pages.
Niimi et al., "Reduced pH and chloride levels in exhaled breath condensate of patients with chronic cough", Thorax: first published as 10.1136/ths.2003.012906 on Jun. 29, 2004, 5 pages.
Pacheco, et al., "Refractory chronic cough, or the need to focus on the relationship between the larynx and the esophagus", Pacheco and Cobeta Cough 2013, 9:10 http://www.coughjournal.com/content/ Sep. 1, 10, 7 pages.
Partial European Search Report for EP 19 88 1312 dated Jun. 28, 2022, 17 pages.
PureHale Technology Platform, Ready to Use Nebulizer Brochure, Apta Pharma, 4 pages.
Resyca, Brochure, 4 pages.
S G Burch et al: "Effect of pH on Nicotine Absorption and Side Effects Produced by Aerosolized Nicotine", Journal of Aerosol Medicine, Nov. 1, 1993 (Nov. 1, 1993), XP055328965.
Samanta, et al., "Store-operated Ca2+ channels in airway epithelial cell function and implications for asthma", Phil. Trans. R. Soc. B 371: 20150424. http://dx.doi.org/10.1098/rstb.2015.0424, 7 pages.
Shei, et al. "The Epithelial Sodium Channel (ENaC) as a Therapeutic Target for Cystic Fibrosis", Curr Opin Pharmacol. Dec. 2018 ; 43: 152-165.
Slinger, et al., "Speech and language therapy for management of chronic cough", Cochrane Database of Systematic Reviews 2019, Issue 7. Art. No. CD013067., 41 pages.
Tanner et al. "Nebulized Isotonic Saline Versus Water Following a Laryngeal Desiccation Challenge in Classically Trained Sopranos", Journal of Speech, Language, and Hearing Research vol. 53, Dec. 2010, pp. 1555-1566.
Thai, et al., "The Polarized Effect of Intracellular Calcium on the Renal Epithelial Sodium Channel Occurs as a Result of Subcellular Calcium Signaling Domains Maintained by Mitochondria", Journal of Bio. Chem. vol. 290, No. 48 pp. 28805-28811, Nov. 27, 2015.
Veldurthy, et al., "Vitamin D, calcium homeostasis and aging", Citation: Bone Research (2016) 4, 16041; 10.1038/boneres.2016.41, 7 pages.

* cited by examiner

FORMULATIONS AND COMPOSITIONS FOR ORTHO- AND/OR RETRO-NASAL DELIVERY AND ASSOCIATED SYSTEMS, METHODS AND ARTICLES

FIELD

This disclosure generally relates to a composition of food, therapeutic and other substances in a form suitable for ortho-nasal and retro-nasal delivery, which may be used to modulate human or other animal metabolic processes or treat medical conditions, and in particular to related formulations, compositions, and related systems, methods, and articles of manufacture.

BACKGROUND

Description of the Related Art

All of our five sense act as messengers that deliver information to the brain, which then processes this information, causing us to respond in relatively predictable ways. Within the context of our sense of smell, all odors present themselves in specific chemical configurations, allowing humans to perceive a wide variety of distinct odors. Odor perception initiates in the nose, where the respective molecules are detected by a large family of olfactory receptors. Olfactory receptors have diverse protein sequences, and are assigned to subfamilies on the basis of sequence relationships. These observations formed the basis for research into the mechanisms underlying human odor perception, leading to the 2004 grant of the Nobel Prize in Physiology and Medicine to Linda B. Buck and Richard Axel.

However, even given the significant importance of our sense of smell, relatively little has been done to develop the apparent physiological value of this sense or to more thoroughly incorporate it into how humans experience the world around them on a daily basis. Although some systems and devices have been proposed for attempting to provide olfactory sensations to users (see, for instance, U.S. Pat. Nos. 8,050,545, 8,032,014, 6,654,664 and 6,803,987), they have proven inadequate as mobile, personal, targeted and effective delivery systems that may be used to alter behavior.

Spices add flavor to food and beverages by binding to receptors and possibly other membrane proteins in the mouth and nose (or generally in the vicinity of the nasopharynx). Binding produces taste, olfactory, heat and other sensations that may produce pleasure among other wellbeing and health benefits. Traditionally spices are added or otherwise integrated into foods and consumed in the act of eating and drinking. Depending on the food form, some fraction of the spices actually binds to receptors in the nasopharynx—to be tasted or smelled. Minute quantities of spices can exist in vapor form, as when one smells ginger over a cup of ginger tea. More generally spices are ingested, and the largest amount swallowed before acting on taste or olfactory receptors—e.g., studies have shown that around 80% of bread is swallowed prior to complete dissolution in the mouth. In some cases the benefits of spices are weighed against untoward effects on ingestion, as in excessive levels of sodium, which can lead to hypertension.

As explained herein, new approaches that effectively deliver therapeutic and other substances in order to elicit a physiological response are desirable.

BRIEF SUMMARY

Recent advances in olfaction biology have made it clear that flavor images that appear in the brain as a consequence of activating sensory receptors in the process of eating and drinking play a role in up- and down-regulating of metabolic function. Among the most important of sensory receptors involved in the creation of these flavor images are olfactory receptors in the nasal epithelium. Other receptor include taste receptors and transient receptor potential vanilloid (TRPV) receptors. Various such receptors appear elsewhere in the body, including the heart, gut, and circulating cells of the immune system. As such, stimulation of TRPV receptor, olfactory receptors, and/or taste receptors can influence not only metabolic processes but other processes including those involved in immunity and brain function.

The delivery of substances (i.e., active substances) to the nasal epithelium to modulate human health, as in the delivery of active substances for relieving congestion, or symptoms related to asthma, generally involves the delivery of dry or liquid formulations to the nose via a nebulizer, metered dose inhaler, or dry powder inhaler. These delivery modalities conventionally involve spraying or sniffing active substances directly into the nose via the nostrils or nasal vestibule.

Active substances deposit in the nose, depending on the nature of the delivery system and technique, with some associated degree of efficiency. This efficiency can be measured as a fraction of “delivered dose” to “nominal dose.” Delivered dose is the mass of active substance that not only deposits on the nasal epithelium, but is delivered to the target tissues and/or receptors. Given that clearance of the active substance from the nose is rapid, delivery to the nose of the dose of active substance in a form that is quickly dissolved and distributed is highly desirable.

Naturally, delivery of odorants (i.e., scent molecules) to the nasal epithelium occurs in two ways. The first, ortho-nasal scent delivery, occurs by sniffing odorants in the atmosphere, e.g., directly via the nostrils or nasal vestibule. The second, retro-nasal scent delivery, occurs by the natural diffusion and convection of odorants in the mouth into the nasal passages via the oropharynx. This latter delivery is referred to as retro-nasal olfaction, and is promoted by exhalation.

It has recently been found that many people who cannot perceive scent via ortho-nasal olfaction, can actually perceive scent or flavor via retro-nasal olfaction. The surprising “special capacity” of retro-nasal olfaction relates to the fact that the human oropharynx is supremely well designed to bring odorants in the mouth into the nasal passages. As a consequence, flavor perception plays a critical role in the regulation of human metabolism. Humans develop likes and cravings for certain foods as a consequence of experiencing the metabolic effects of these foods, and associating these effects with flavor images in their brains. Eventually, these images, as memories (the olfactory nerve links olfactory receptors in the nose with the seat of long-term memory, the hippocampus) drive food interests and cravings that lead to humans receiving the metabolic effects they enjoy.

Recently, human and animal studies have found that simply perceiving the scent of certain foods, like chocolate or the aroma of roasted coffee beans, can trigger metabolic effects that heretofore have been believed to occur only on the ingestion of chocolate or coffee. This surprising finding, combined with the discovery of the general efficacy of retro-nasal olfaction versus ortho-nasal olfaction, opens up a completely new opportunity for active substance (e.g., drugs, and various scent molecules that have until now principally been understood to relate to food and flavor perception) delivery to the nose.

Described herein are new formulations and compositions, and associated apparatus, methods and articles for delivery of active substances ortho-nasally or retro-nasally to target TRPV receptors, olfactory receptors, and/or taste receptors. The described compositions, apparatus, methods and articles can be employed for the up- and down-regulation of human (and other animal) metabolism, as well as to other beneficial physiological effects. Rather than limiting delivery of active substances to the nose via the standard ortho-nasal route, the described approaches advantageously deliver active substances to the nose via the retro-nasal route. The active substances are formulated in readily-soluble water droplets that have a median size range of 2-50 microns, 5-20 microns, or 6-10 microns, advantageously too large for significant penetration into the lungs, while small enough to be carried into the nose.

Disclosed herein are compositions and methods for delivering spices and other food or therapeutic substances to the oropharynx with much greater efficiency of receptor binding and minimal ingestion into the stomach. According to various embodiments, it is possible to deliver spices and other food and therapeutic substances such as salts, pepper, cinnamon, ginger, thyme, mints, electrolytes, among others in a way that delivers meaningful food and therapeutic sensations and effects while with mass quantities that are far lower than normally needed to effectively spice a particular food or drink to be ingested. These spices can be delivered with nutrients, therapeutic substances and other foods and they can also be experienced independently of consuming food and drink, as well.

Thus, various embodiments are directed to concentrating aqueous or mixed water/alcohol solutions with spice compositions, that can be delivered to the oropharynx independently of consuming food or drink, or in the act of eating or drinking the spiced solution—as small (100 microns or smaller, and preferable 50 microns or smaller, or especially preferably 20 microns or smaller, with mass median size of approximately 5 or 6 microns to up to 20 microns) droplets into the mouth and/or the nose. These droplets deposit along the inner surfaces of the mouth and nose and possibly enter the airways. Given that the mass of each droplet is extremely small, the probability of contact between a spice molecule in the droplet and a receptor in the mouth or nose is far higher than were the molecule delivered in a piece of bread, a glass of water, or any other macroscopic food or drink form. A typical cloud of droplets delivered into the mouth or nose, either by smelling a cloud suspended before the nose, or in the act of eating a food or drinking a beverage (smelling, eating and/or drinking collectively referred to herein as imbedding), is around 10 micrograms to several hundred micrograms. The mass of spices in the droplets of the cloud is approximately 1/100th of the mass of the cloud itself, meaning the total mass of spice delivered can be on the order of 100 nanograms to several micrograms. Consuming a glass of water with salty Coke-flavored clouds may involve therefore around 1 microgram of sodium while drinking a can of Coca Cola may lead to ingestion of around 64 milligrams of sodium.

Minimally the compositions contain one or more active ingredients that act on a taste and—or—olfactory receptor and possibly on a heat sensation protein, such as TRPV1 (for heat sensation), TRPV3 and TRPV4 (for warmth sensation) and TRPV8 (for cold sensation). Ideally they act on two of the three, and especially optimally they act on all three—that is a spice composition contains active ingredients that act on at least one taste receptor, at least one olfactory receptor, and at least one heat sensation protein. Since a very small quantity of spice composition is delivered, it is beneficial in terms of the significance of the degree of physiological reaction, to trigger more than one sensation, and this multiplicity of sensations can be critical to the effect.

Further information on TRP channels, TRVP receptors, and target therapies may be found in: Holzer, "Transient receptor potential (TRP) channels as drug targets for diseases of the digestive system," *Pharmacology & Therapeutics* 131:142-170, 2011; Jia et al., "Role of TRPV receptors in respiratory diseases," *Biochimica et Biophysica Acta* 1772:915-927, 2007; and Morelli et al., "TRP Channels: New Potential Therapeutic Approaches in CNS Neuropathies," *CNS & Neurological Disorders Drug—Targets* 12, 2013, all of which are herein incorporated by reference.

As also described herein, apparatus are provided which allow the portable, discrete delivery of active substances, enhancing or efficiency of delivery to humans and other animals. Advantageously, the apparatus is configured to be portable, allowing the user to have the benefit of retro-nasal delivery, on demand, in a wide variety of environments. The apparatus and compositions may be used to enhance the efficiency of delivery of active substances, and to provoke a physiological response in a human or other animal via the connection of the olfactory sensory system.

In some implementations, a device is provided which takes the form of a primary vessel or at least includes a primary vessel portion with one or more docks, to which one or more distinct delivery devices (e.g., nebulizers) is dockable to dispense aerosol into an interior of the primary vessel portion, which allows retro-nasal ingestion of the aerosol The distinct delivery devices (e.g., nebulizers) or outlet (e.g., port, nozzle) thereof may be positioned and oriented so that a spray or other distribution of scent media is directed towards, and optionally against, a bottom inner surface of the primary vessel, to advantageously ensure that the dispensed media at least initially stays in the interior of the vessel, for instance until sampled or "ingested" by a human end user. The vessel may have an opening, for example at a top of a neck or chimney. In some implementations, one or more covers are provided, the cover removably securable to close the docks of the primary vessel, for example when no distinct delivery device is coupled thereto. Alternatively, one or more docks can be left open, and used as a carburetor, a user sliding a finger across to selectively alternatingly provide and deny access to an interior of the vessel from an exterior thereof via the opening. The nebulizer may include a screen and a piezo-electric element, solenoid, or an electric motor physically (e.g., mechanically, magnetically) coupled to move (e.g., oscillate, rotate) the screen and thereby cause dispersion of the media in the interior of the vessel, for instance as a spray.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 2:
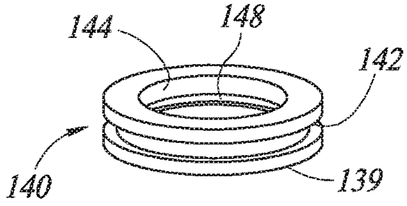
FIG. 2 is an isometric view of a dock of the delivery system, in the form of a gasket with a pair of opposed peripheral channels.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with microcontrollers, piezo-electric devices, Peltier devices, power supplies such as DC/DC converters, wireless radios (i.e., transmitters, receivers or transceivers), computing systems including client and server computing systems, and networks (e.g., cellular, packet switched), as well as other communications channels, have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

In particular, described herein are new compositions, systems, methods, and articles of manufacture to advantageously delivery of one or more active substances to the nose via retro-nasal delivery. Such can be employed in the up-regulation and, or, down-regulation of human and other animal metabolism. Such can additionally or alternatively be employed to produce other beneficial physiological effects, for example decongestion. Rather than limit delivery of active substances to the nose via the standard ortho-nasal route, the compositions, apparatus, methods and articles described herein advantageously deliver active substances to the nose via the retro-nasal route.

These active substances or compositions are advantageously formulated as or in readily-soluble water droplets. The readily-soluble water droplets have a median size range of approximately 2, 5 or 6 microns to approximately 50, 20, or 10 microns. Thus, the readily-soluble water droplets are too large for significant penetration into the lungs, while being small enough to be carried into the nose.

The active substances can be dissolved, if water soluble, directly in the water droplets. The active substances can, for example if not water soluble, be encapsulated inside, or otherwise formulated as, micelles, micro-emulsions, emulsions, liposomes, nanoparticles or other kinds of colloids. These colloids do not have a size larger than 500 nm, and optimally 200 nm or smaller. The small size of these colloids permits the nebulization of the droplets without destroying the colloids or otherwise impeding (e.g., clogging) the nebulizer (e.g., ultrasound transducer).

The droplets are delivered as aerosol to the mouth, for instance by the act of sipping. Sipping can either involve simply placing one's lips in a cloud of droplets containing the active material and sipping, or involve taking the droplets into the mouth via a conduit (e.g., a straw). On sipping the aerosol or cloud, the droplets are delivered to the mouth where the droplets are suspended in the air in the mouth, and settle by gravity. The vapor around the droplets can immediately bring active substance into the nose via a "chimney effect" of the nose, and the droplets will themselves waft into the nose and deposit there, delivering active substances in a form that quickly acts on or within active tissue and resists quick clearance. Notably when the active substances are in small colloidal (e.g., nanoparticle) form, the colloids will themselves tend to resist clearance whereas larger particulates than those encompassed by the compositions described here will tend to be cleared through mucocilliary action. The active-substance-loaded droplets described here are produced from a small reservoir of less than 100 ML, optimally less than 50 ML, and particularly optimally less than 25 ML.

The composition, apparatus, methods and articles described herein have various useful benefits. The delivery of active substances or compositions (e.g., odorants or flavorful molecules of some kind, or other more traditional therapeutics) that up- and down-regulate metabolism, can be achieved with less than 1 gram of ingested active substance or composition. That is, the approaches described herein can deliver active substances to transient receptor potential vanilloid (TRPV) receptors, and/or to olfactory receptors and/or taste receptors, producing physiological benefit (e.g., up-regulating and, or down-regulating human metabolism), while delivering almost no active substance to the gastrointestinal (GI) tract. Second, for the purposes of delivery solely to the nose, the approaches described herein can produce greater physiological effect per nominal dose delivered to the nose than any other approach known by applicants, as in a spray or respiration from the environment into the nose.

Other kinds of water aerosols that are delivered to the mouth include electronic cigarettes and a methodology known as "Le What." Electronic cigarettes nebulize material into the mouth however with particle sizes that are small enough to penetrate the lungs and via the act of respiration, not sipping. Le Whaf produces mean particles sizes that are larger than 50 microns, thus not optimally suited to penetration into the nose. Other kinds of retro-nasal delivery of active substances exist in the form of highly volatile or aromatic lozenges, or food and drink, as in chocolate cake or a cup of coffee. These latter all involve ingested material with nominal masses placed in the mouth of greater than 1 gram.

Figure 1:
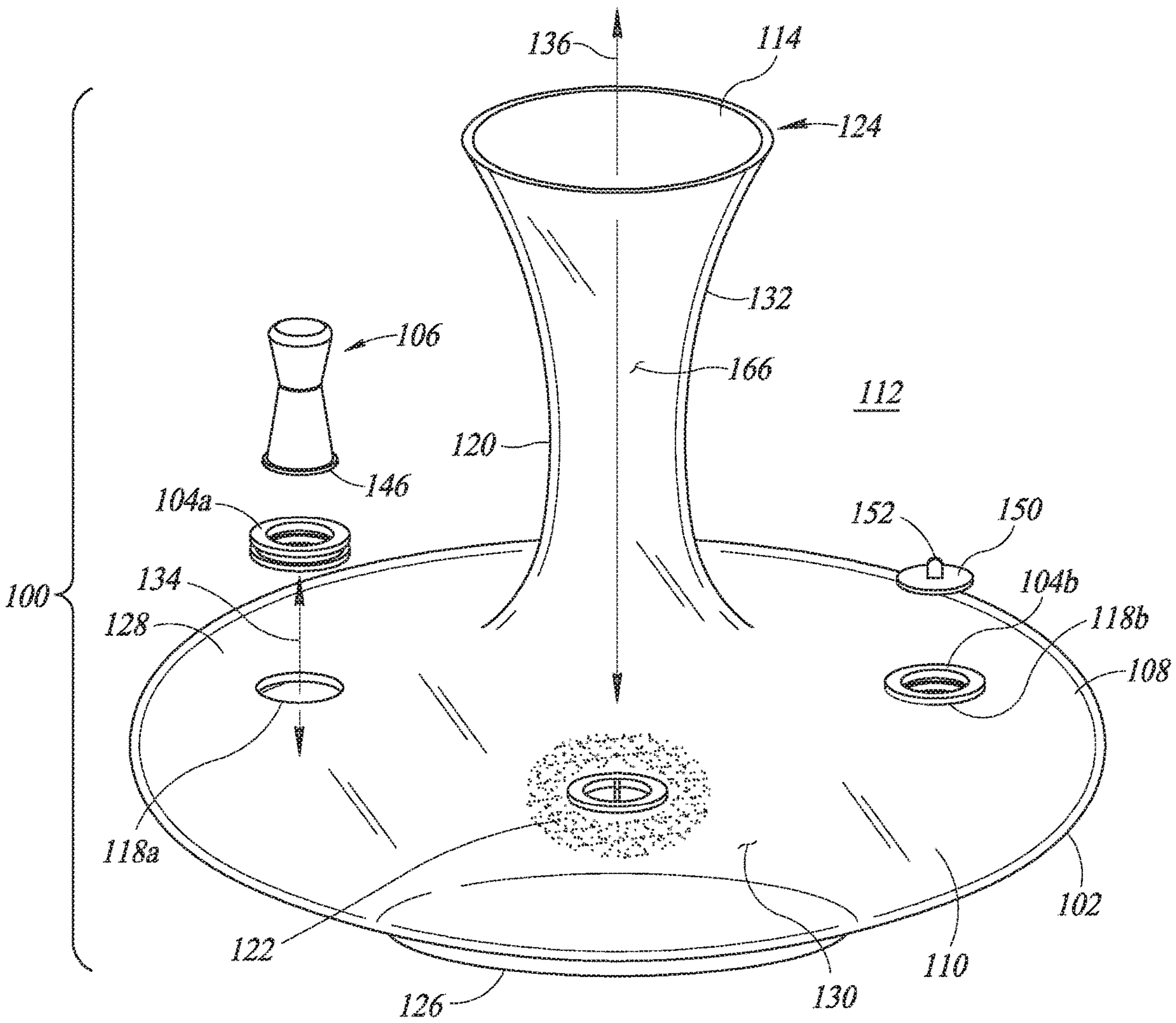
FIG. 1 is an isometric, partially exploded view of a delivery system according to at least one illustrated implementation, including a primary vessel, a plurality of docks, and at least one distinct delivery device selectively dockable to the primary vessel via one of the docks and operable to dispense an aerosol into an interior of the primary vessel for ingestion by a person or other animal.

FIG. 1 shows a delivery system 100, according to at least one illustrated implementation.

The delivery system 100 includes a primary vessel 102, a plurality of docks 104*a*, 104*b* (only two called out, collectively 104), and at least one distinct delivery device 106 (only one illustrated), the at least one distinct delivery device 106 removably dockable to the primary vessel 102 via the docks 104.

The primary vessel 102 includes at least one wall 108 which, at least partially, delimits an interior 110 of the primary vessel 102 from an exterior 112 thereof. The primary vessel 102 may be comprised of a solid material, such as a hard plastic, acrylic, ceramics, glass, or other similar material. The primary vessel 102 has an outlet port 114 that provides a fluidly communicative path 116 between the interior 110 of the primary vessel 102 and an exterior 112 thereof. The primary vessel 102 further having a plurality openings 118*a*, 118*b* (two shown, collectively 118) that each provide a respective passage through the at least one wall 108 between the exterior 112 and the interior 110 of the primary vessel 102. The primary vessel 102 may, for example, form a chimney 120. The interior 110 of the primary vessel 102 temporarily retains the aerosol 122 formed by the at least one distinct delivery device 106 when docked thereto and operated to form the aerosol 122. The outlet port 114 of the primary vessel 102 is sized and dimensioned to accommodate a portion of a nose including two nostrils.

The primary vessel 102 has a top 124, and the outlet port 114 of the primary vessel 102 is positioned at least proximate the top 124 of the primary vessel 102, and the at least one distinct delivery device 106 is positioned relatively below the top 124 of the primary vessel 102. The primary vessel 102 may have a bottom 126, on which the primary vessel 102 may sit or rest. The distinct delivery devices 106, or a portion (e.g., nozzle) of each of the distinct delivery devices 106, is oriented to dispense the aerosol 122 toward the bottom 126 of the primary vessel 102.

For example, the primary vessel 102 may have an upper surface 128 disposed above the bottom 126 and disposed across the interior 110 from the bottom 126 to form a chamber 130, and a neck 132 that extends upwardly from the upper surface 128, the outlet port 114 at an end 134 of the neck 132. The neck advantageously acts as a spacer between the chamber 130, which holds the aerosol, and the outlet port 114.

The openings 118 may be advantageously located in the upper surface 128, with the docks 104. When docked, the at least one distinct delivery device 106 or a portion thereof is oriented to dispense the aerosol 122 downward at an angle perpendicular to the bottom 124 of the primary vessel 102 or within 12 degrees of perpendicular, for example along a principal axis 134 that is parallel to a longitudinal axis 136 of the neck 132. A user can sip, imbibe, or otherwise consume the vaporized media or media in aerosol form from the primary vessel 102 by positioning their mouth at the outlet port 114 and consuming the scent media via the outlet port 114.

The distinct delivery devices 106 are preferably removably dockable to the primary vessel 102 via the at least one the docks 104 thereof. When docked, some portion or all of the distinct delivery device 106 may be located within the interior portion 110 of the vessel 102. The distinct delivery devices 106 respectively comprise a reservoir, an actuator, and control subsystem communicatively coupled to control the actuator. The reservoir which at least in use holds active substance media. Alternatively, the distinct delivery devices 106 may include a respective a media reservoir holder that in use removably holds at least one media cartridge that contains a therapeutically effective measured dosage of the active substance media. The actuator is controllably operable on the active substance media to cause formation of an aerosol comprising readily-soluble droplets have a median size range of approximately 2 microns to approximately 10 microns and comprising the one or more active substances. The readily-soluble droplets may, for example, take the form of water droplets. The active substance may, for example, be dissolved in the water droplets. The active substance may, for example, be entrained in the aerosol. The active substance may, for example, be in the form of readily-soluble droplets of the active substance. The active substance may, for example, be encapsulated inside the droplets.

A chamber of the distinct delivery device 106 is fluidly coupleable to the interior 110 of the primary vessel 102 when the at least one distinct delivery device 106 is coupled to the vessel via one of the docks 104. For example, a nozzle of the distinct delivery device (not visible in FIG. 1) may provide a fluidly communicative passage between chamber of the distinct delivery device 900 and the interior 110 of the primary vessel 102 when the distinct delivery device 900 is docked.

Figure 3:
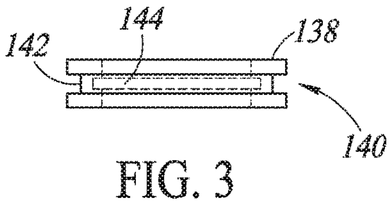
FIG. 3 is a side elevational view of the dock of FIG. 2.
Figure 4:
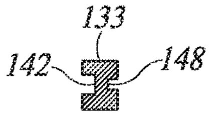
FIG. 4 is a cross-sectional view of a portion of the dock of FIGS. 2 and 3, better illustrating the opposed peripheral channels.

Each dock 104 is associated with a respective one of the openings 118 of the primary vessel. The docks 104 allow the distinct delivery devices 106 to be physically coupled, secured or docked to the primary vessel 102, and preferably physically uncoupled or undocked. The docks 104 may take a variety of forms. For example, the docks 104 may take the form of annular gaskets 138. As best illustrated in FIGS. 2, 3 and 4, the gaskets 138 each have an outer periphery 140 (e.g., an outer diameter) that is sized (e.g., radial dimension) and shaped (e.g., circular) to be closely received in a respective hole of the primary vessel 102. The gaskets 1238 may include an outer channel 142 that extends about the outer periphery 140 thereof, sized (e.g., outer diameter, height) and shaped to receive an edge of the wall 108 of the primary vessel 102 that forms the respective hole 118. The gaskets 138 each have an inner periphery (e.g., an inner diameter) 144 that is sized (e.g., radial dimension, height) and shaped (e.g., circular) to closely receive in a portion (e.g., edge, lip or plate 146 (FIG. 1)) of a respective one of the distinct delivery devices 106. The gaskets 138 may include an inner channel 148 that extends about the inner periphery 144 thereof, sized and shaped to securely detachable receive the outwardly extending edge, lip or plate 146 of the distinct delivery device 106.

Returning to FIG. 1, the delivery system 100 may include one or more plugs 150, which are removably coupleable, securable or dockable to the primary vessel 102 via the docks 104. Such may removable plug the holes 118 associated with the docks 104 to seal the holes 118 and docks 104 when no distinct delivery device 106 is docked thereto. The plugs 150 may have an outer perimeter sized (e.g., outer diameter, height) and shaped to be received by the dock (e.g., received by inner channel 148 of gasket 138). The plugs 150 may have a handle or pull 152 to facilitate removal or undocking.

In some uses, two or more distinct delivery devices 106 may be docked at respective docks, and operated sequentially to provide a sequence of aerosol clouds in the interior 110 of the primary vessel 102, or operated concurrently to provide a combined aerosol cloud in the interior 110 of the primary vessel 102, combined aerosol cloud mixing two or more media. The distinct delivery devices 106 may be operated to achieve a defined ratio between two or more media.

Figure 5:
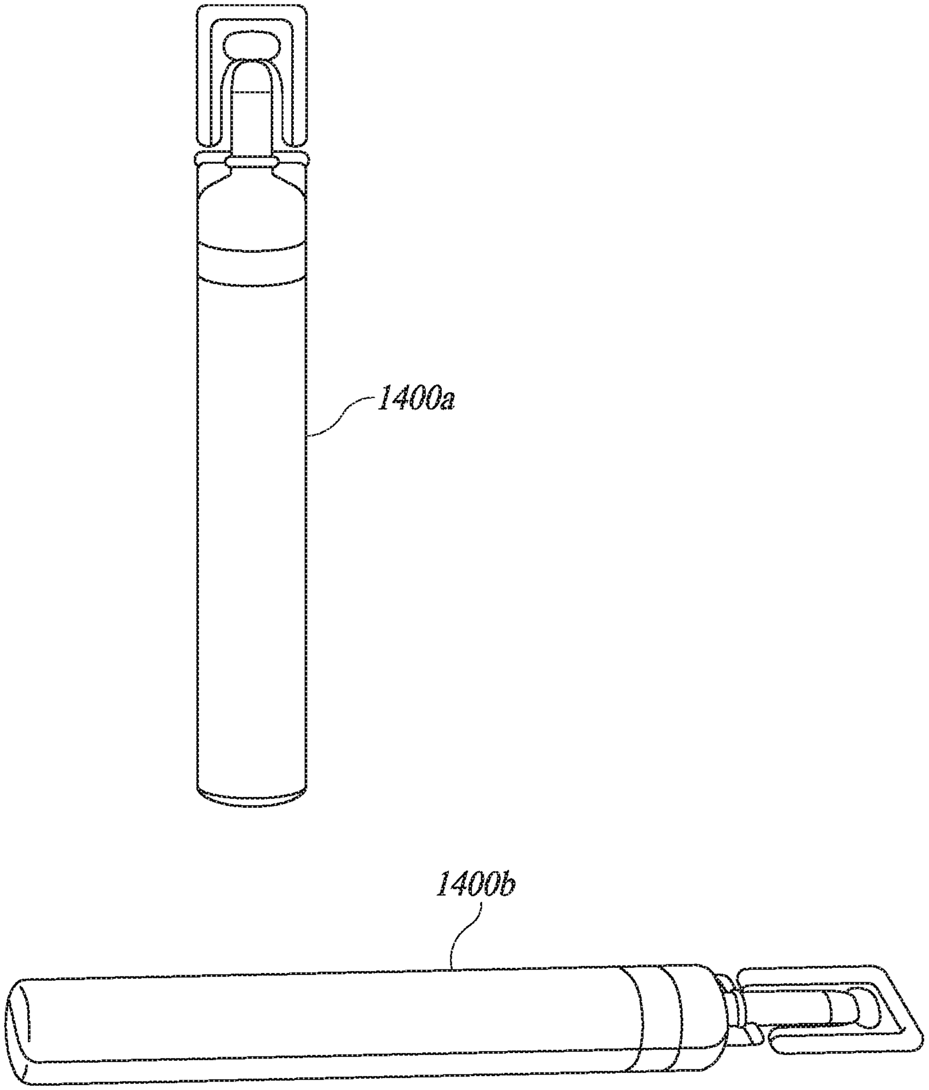
FIG. 5 is an isometric view of a pair of cartridges that carry scent media and which are sized and dimensioned to be removably receivable by a scent media reservoir to supply scent media via the nebulizer, according to at least one illustrated implementation.

FIG. 5 shows a portion of the distinct delivery device 900 according to at least one illustrated implementation. The distinct delivery device 900 may take the form of, or otherwise include, a nebulizer 1002, with one or more actuators 1004, and a control subsystem 1006 and, or other electronics, according to at least one illustrated implementation.

The nebulizer 1002 can include one or more mesh screens 1008, for example a metal mesh screen, which is supported by a frame 1010 for movement, for example for oscillation or rotation The nebulizer 1002 can include one or more of a piezo-electric element 1012, solenoid 1014 or electric motor 1016 physically coupled to move the mesh screen(s) 1008 along at least one axis in response to signals from the microcontroller to dispense aerosol into the chamber. In some implementations, the actuator is physically coupled to the mesh screen 1008 via one or more mechanical transmissions (e.g., elliptical gear) or magnetic transmissions. The nebulizer may, for example, oscillate the screen at ultrasonic frequencies to cause a dispersion of the scent media. The transducer may oscillate at a frequency of about 175 kHz±5 kHz that is sufficient to atomize the fluid held in the fluid reservoir. The frequency of oscillation of such a transducer may be increased or decreased depending up on the properties of the fluid or other materials held within the fluid reservoir. In such an implementation, that transducer may form an annular ring with a metal-mesh included within a center portion of the transducer. In some implementations, the metal-mesh screen 1008 may be fluidly coupled to the fluid reservoir via capillaries, thereby providing a fluid path that enables a low flow of the fluid from the fluid reservoir to the metal-mesh screen 1008. As such, the fluid may be transported to the metal mesh, via, for example, capillary action, where it is atomized into the vapor or aerosol as a result of the oscillation of the transducer. In some implementations, the metal-mesh screen 1008 may provide a filter that prevents large sized molecules from being emitted as part of the vapor or aerosol that enters the interior portion of the primary vessel 102 (FIG. 1). As such, the metal-mesh screen 1008 may have mesh openings that are 500 micrometers in width. In some implementations, the mesh openings may be less than 500 micrometers in width (e.g., 100 micrometers, 200 micrometers, 300 micrometers, or 400 micrometers). Preventing the larger molecules from being introduced into the interior portion of the primary vessel 102 may provide for a better user experience by reducing the possibility that the vapor or aerosol will irritate the user.

The actuators 1004 may include one or more of radios 1018, transducers or sensors 1020 and, or, switches 1022 communicatively coupled to the control subsystem 1006.

The control subsystem 1006 may, for example, include one or more microcontrollers 1024, microprocessors, field programmable gate arrays, and, or application specific integrated circuits. The control subsystem 1006 may, for example, include one or more nontransitory storage media 1026 that stores at least one of processor-executable instructions or data, which when executed by the microcontroller 1024 causes the microcontroller 1024 to control operation of the device 900, for example in response to one or more inputs. For example, the microcontroller may receive signals from one or more of radios 1018, transducers or sensors 1020 and, or, switches 1022, and control operation of the nebulizer 1002 in response to same. For instance, the control subsystem may cause the nebulizer to dispense or disperse scent media in response to a first input, and to stop the nebulizer from dispensing or dispersing scent media in response to a second input. Input can include user manipulation of a switch, positioning or orientation of the vessel by the user, or wireless commands from a radio or remote controller.

The distinct delivery device 106 may, for example, include one or more switches and/or sensors. The switch(es) and/or sensor(s) may be communicatively coupled to the microcontroller and operable to produce a signal that causes the microcontroller to operate the actuator accordingly. The switches may, for instance, include one or more of any of the following: a contact switch, a momentary contact switch, a rocker switch, etc. The sensors may, for instance, include one or more of any of the following: The device may, for example, include one or more sensors, for instance a one-, two- or three-axis accelerometer, a PIR motion sensor, an inductive sensor, a capacitive sensor, and, or Reed switches. The switch(es) and/or sensor(s) may, for example, be operable to produce a signal that causes the microcontroller to operate the actuator in response to the at least one distinct delivery device 106 being coupled to at least one of the docks. The switch(es) and/or sensor(s) may, for example, be responsive to a presence or an absence of the vessel with respect to a base and operable to produce a signal that causes the microcontroller to operate the actuator according to the presence or an absence of the vessel with respect to the base. The switch(es) and/or sensor(s) may, for example, be responsive to a position or orientation of the vessel and operable to produce a signal that causes the microcontroller to operate the actuator according to the orientation of the vessel. The switch(es) and/or sensor(s) may, for example, be part of the at least one distinct delivery device.

The distinct delivery device 106 may include a transducer communicatively coupled to operate the nebulizer. The transducer may, for example, include one or more radios (e.g., cellular transceiver, WI-FI transceiver, Bluetooth transceiver) which receives wireless signals for instance RF or microwave signals for one or more wireless communications devices (e.g., smartphones) or remote controllers. The transducer may, for example, include one or more receivers, for instance an infrared receiver that receivers infrared light signals from a remote controller.

Activation may be synchronized with the delivery of audio, video, or audiovisual media. For example, a smartphone or digital assistance (e.g., Amazon Alexa®, Google Home®, Apple HomePod®) can cause activation of flavorful droplets inside a vessel that a consumer can experience in coordination with the delivery or experience of other digital media, e.g., music, film, video games, virtual reality (VR), augmented reality (AR), etc.

A suitable microcontroller may take the form of an 8-bit microcontroller with in-system programmable flash memory, such as the microcontroller commercially available from Atmel Corporation under designation ATMEGA48/88/168-AU. The microcontroller executes a program stored in its memory, and sends signals to control the various other components, such as, for example, the valves. Control signals may, for instance be pulse width modulated (PWM) control signal, particularly where controlling an active power supply device. Otherwise, control signals may take on any of a large variety of forms. For instance, the microcontroller may operate valves or the actuator 1004 simply by completing a circuit that powers the respective value or actuator 1004.

The distinct delivery device 106 may optionally include a visual indicator (not illustrated) to indicate when the distinct delivery device 106 is operating or turned ON. Although a single light emitting diode (LED) may be employed, the visual indicator may take any of a large variety of forms. The LED may be capable of emitting one, two or more distinct colors. The visual indicator may also indicate other information or conditions, for instance the visual indicator may flash in response to an occurrence of an error condition. A pattern of flashes (e.g., number of sequential flashes, color of flashes, number and color of sequential flashes) may be used to indicate which of a number of possible error conditions has occurred.

In some implementations, the distinct delivery device 106 is electrically powered by one or more batteries that may provide a power source for the oscillation of the actuator 1004. The battery may be small and lightweight, such as the batteries used for small electronic devices (e.g., hearing aids). In some implementations, the battery is at least partially embedded within the distinct delivery device. In some implementations, the battery is selectively removable and replaceable, such as when the battery can no longer provide sufficient charge to operate the distinct delivery device 106. Other types of power sources may be provided, such as a power source comprised of one or more photovoltaic panels and associated components that may convert light into energy that can be used to operate the distinct delivery device 106, an array of super- or ultra-capacitor cells, or an array of fuel cells.

Figure 6:
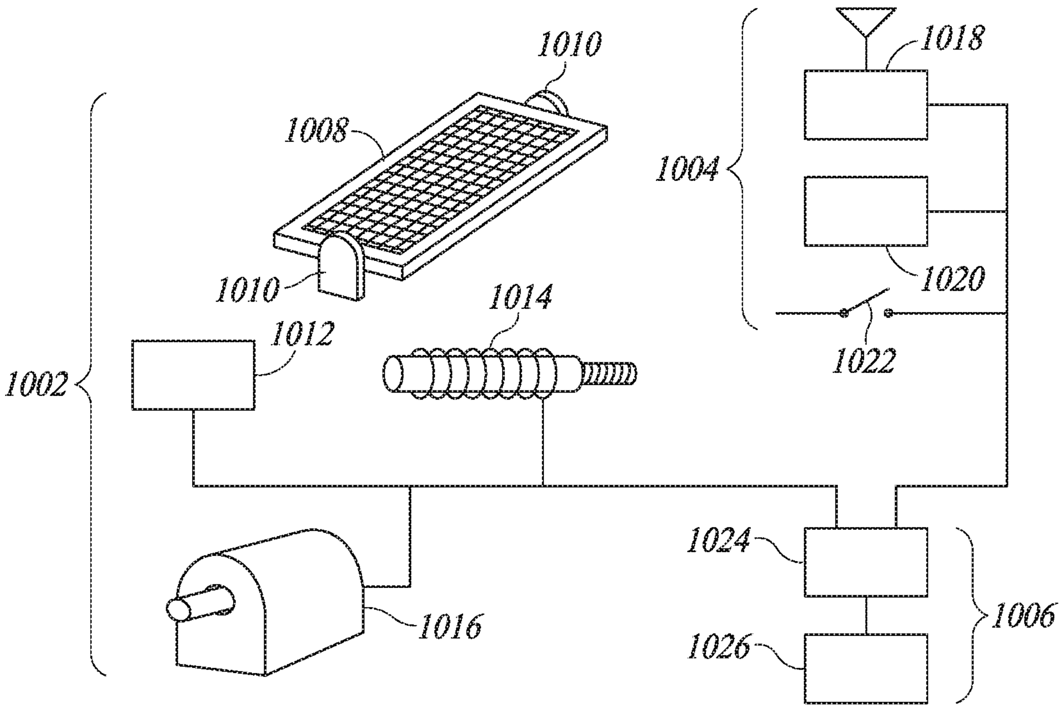
FIG. 6 is schematic view of a portion of a distinct delivery device, including a nebulizer which can include a screen and at least one of a piezo-electric element, solenoid or electric motor physically coupled to move the screen, the device also including one or more of a radio, a transducer or sensor and a switch communicatively coupled to a control system, for example a microcontroller and memory, and operably coupled to control operation of the nebulizer, according to at least one illustrated implementation.

FIG. 6 shows a pair of cartridges **1400*a*, 1440*b* that carry substances to be dispensed, according to at least one illustrated implementation. The cartridges 1400*a*, 1440*b* are sized and dimensioned to be removably receivable by a scent media reservoir of a distinct delivery device 100, 900, to supply media to the nebulizer for dispersion, for example as a spray of droplets or an aerosol. The cartridges 1400*a*, 1440*b* may be made of plastic. Single use cartridges 1400*a*, 1440*b*** may, for example contain a single dose of the substance to be dispensed, stored in a liquid form.

The cartridges 1400 may form a fluid reservoir 104 and may be comprised of a polymer, elastomer, or other lightweight, durable material that may be used to hold a liquid. The cartridges 1400 may be formed of one or more plastics, for example an ABS or polycarbonate plastic. The plastic may be injection molded or vacuum molded to form the cartridges 1400. The type of material or process employed to form the cartridges 1400 from the material should not be considered limiting. In some implementations, the cartridges 1400 may include an interior cavity that forms the fluid reservoir that may be used to hold and contain one or more active substances as a fluid or other material (e.g., powder, gel, colloidal suspension) that carries active substances (e.g., scent molecules). In some implementations, for example, the fluid reservoir may be sized and dimensioned to hold up to 100 mL of the fluid. In some implementations, the fluid reservoir may be sized and dimensioned to hold a maximum amount of the fluid that used to form a single dose, which may, for example, hold less than 100 mL (e.g., 5 mL, 10 mL, 20 mL, 40 mL, or 50 mL). The fluid may be any liquid or other material that is, or that carries, the active substance(s) (e.g., scent molecules) that are released when the fluid transitions to a vapor or aerosol and is released into the interior portion 110 of the primary vessel 102. The cartridges 1400 may include an aperture that forms part of the fluidly communicative active substance path for the fluid to be transferred from the fluid reservoir to the a nebulizer to be converted into a vapor or aerosol. The vapor or aerosol may advantageously comprise readily-soluble water droplets have a median size range of approximately 2 microns to approximately 50, 20, or 10 microns. Thus, the readily-soluble water droplets are too large for significant penetration into the lungs, while being small enough to be carried into the nose. The vapor or aerosol may result in a physiological response from some users when those users encounter the active substance(s) transported by the vapor or aerosol 128.

Figure 7A:
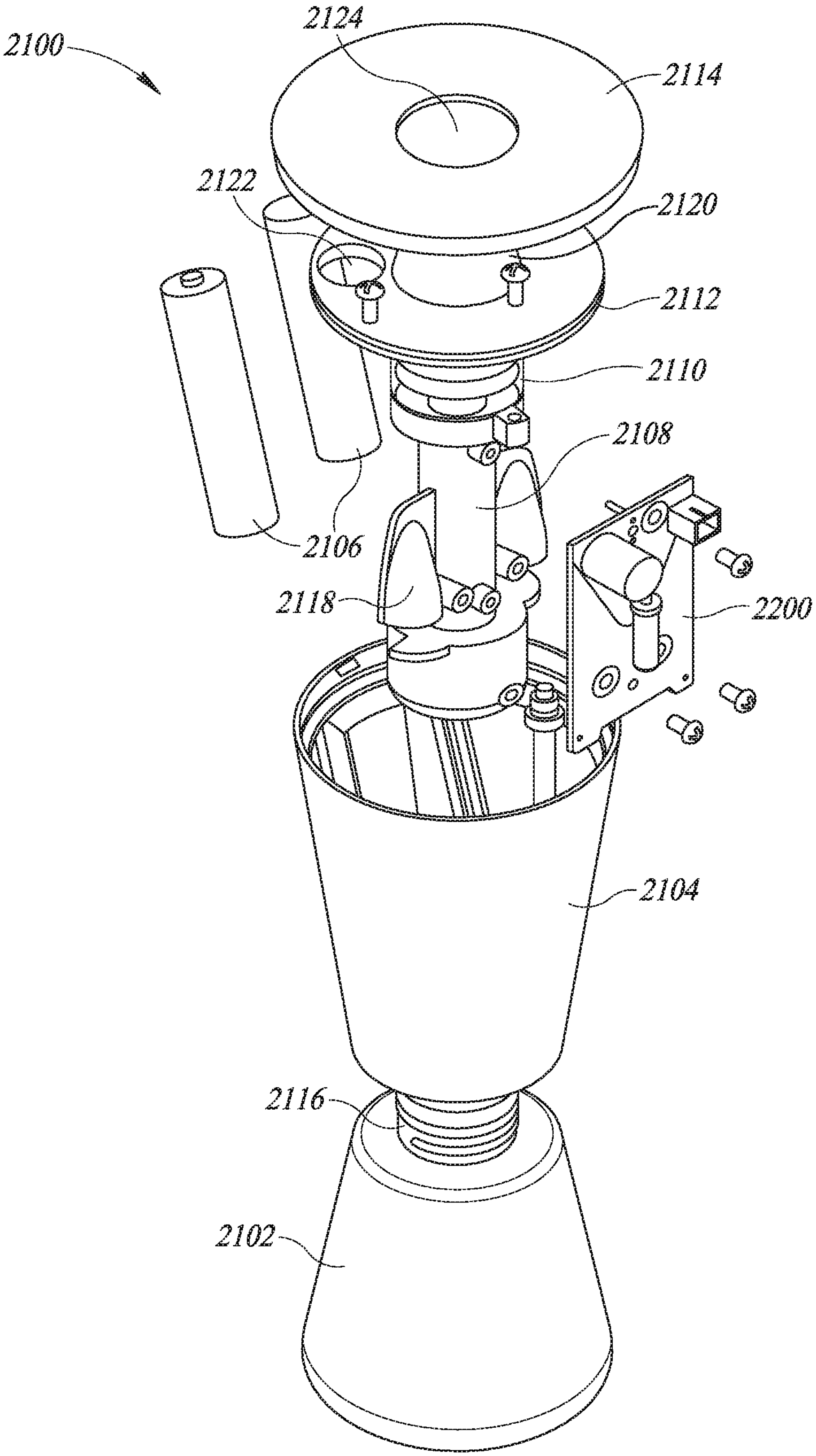
FIG. 7A is an exploded view of a delivery device to deliver a vapor, a cloud, or an aerosol comprising scent media, according to at least one illustrated embodiment.

FIGS. 7A-7F illustrate various views of a handheld delivery device 2100 for producing and delivering a cloud of vaporized scent media or scent media in aerosol form. The device 2100 can include any of the features of any of the other devices described herein, such as the devices 1800 and 1900, and can be used in combination with any of the other devices described herein, such as the device 2000. As illustrated in FIG. 7A, delivery device 2100 includes a base 2102, which can be transparent and which includes a hollow container or tank or vial, in some cases having a volume or capacity of less than 100 mL, for holding scent media in a liquid form. The base 2102 also includes an upwardly-extending hollow conduit, tube, or pipe 2116, through which the scent media can be poured out of the base 2102 in a liquid form. An exterior surface of the conduit 2116 includes a set of threads.

The delivery device 2100 also includes a top or upper portion or main body 2104, which includes a hollow housing and the electronic and mechanical components of the delivery device 2100. Such components include a printed circuit board 2200 and associated components coupled thereto, a pair of batteries 2106, a hollow conduit, tube, or pipe 2108, a piezo-electric device 2110, which can include or be physically coupled to a mesh screen having a mesh size of 3 microns, of 4 microns, of 6 microns, of 20 microns, or of between 3 and 20 microns, as well as an internal cover 2112, and an external cover 2114, which can be transparent or translucent. The housing of the main body 2104 can be opaque or translucent, and can have a specific color such as red, orange, yellow, green, blue, purple, brown, black, or white. The internal cover 2112 can have an appearance matching that of the housing of the main body 2104. In particular, the internal cover 2112 can be opaque if the housing of the main body 2104 is opaque or translucent if the housing of the main body 2104 is translucent, and can have a specific color matching that of the housing of the main body 2104, such as red, orange, yellow, green, blue, purple, brown, black, or white.

The conduit 2108 includes a relatively wide top end portion, a relatively narrow middle portion and a relatively wide bottom end portion sized to extend around the conduit 2116 of the base 2102. An inner surface of the bottom end portion of the conduit 2108 includes threads complementary to the threads of the conduit 2116 so that the conduits 2108 and 2116 can be threadedly engaged and thereby coupled to one another. When the conduits 2108 and 2116 are coupled to one another, liquid scent media can be poured out of the base 2102 through the conduit 2116 and into the conduit 2108. The relatively wide top end portion of the conduit 2108 is sized and configured to house the piezo-electric device 2110 at the top end of the conduit 2108, so that the liquid scent media can flow through the conduit 2108 from the bottom end portion thereof to the piezo-electric device housed at the top end portion thereof.

The conduit 2108 also includes a pair of flanges 2118 that are coupled to opposing outer side surfaces of the middle portion of the conduit 2108, and that extend laterally outward from the respective side surfaces as well as in a direction aligned with the overall length of the conduit 2108. The flanges 2118 each include a recess or cradle that is shaped and configured to cradle a portion of one of the batteries 2106, to partially restrain the batteries 2106 when the device 2100 is assembled. The internal cover 2112 includes a generally circular or disk-shaped main body portion and a hollow and truncated cone-shaped portion 2120 that extends upward from the main body portion. The main body portion of the internal cover 2112 includes a pair of openings or apertures 2122 that extend through the main body portion, Each of the apertures 2122 is sized and configured to cradle a portion of one of the batteries 2106, to partially restrain the batteries 2106 when the device 2100 is assembled. The external cover 2114 includes a generally circular or disk-shaped main body portion and an opening or aperture 2124 that extends through the main body portion. The aperture 2124 is sized and configured to fit snugly around a portion of the outer surface of the cone-shaped portion 2120 of the internal cover 2112 when the device 2100 is assembled.

Figure 7C:
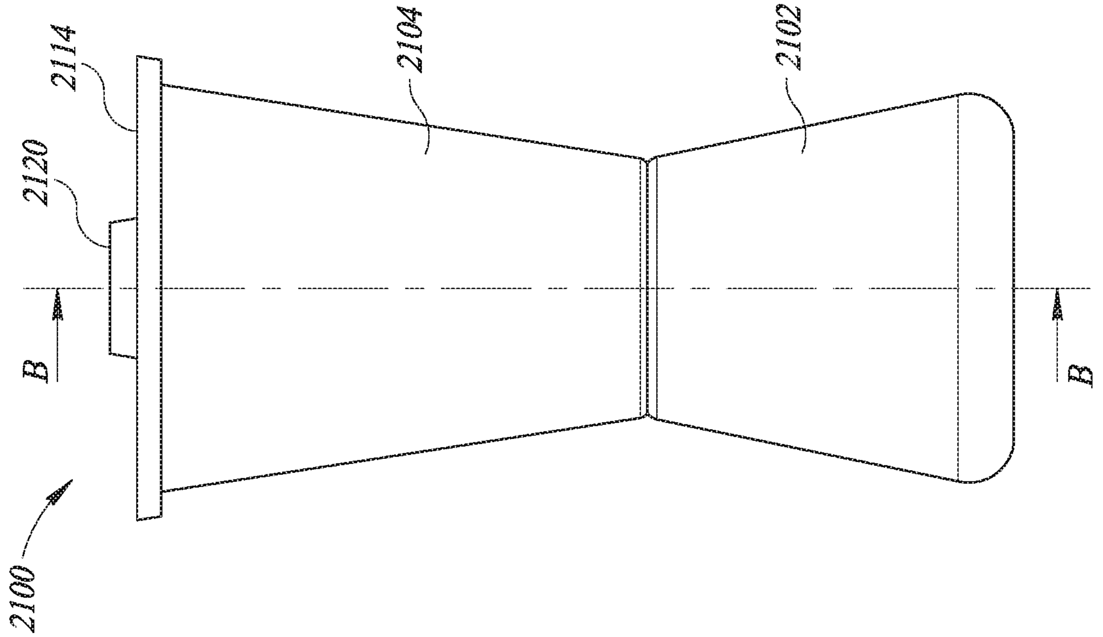
FIG. 7C is a side view of the delivery device to deliver a vapor, a cloud, or an aerosol comprising scent media of FIGS. 7A and 7B, according to at least one illustrated embodiment.
Figure 7B:
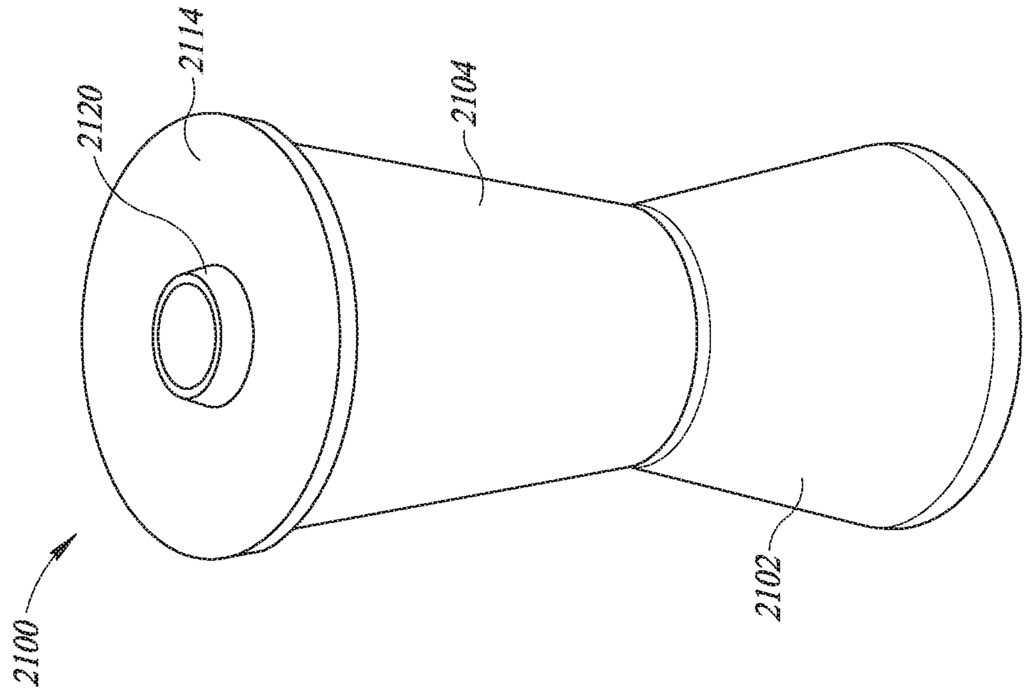
FIG. 7B is a perspective view of the delivery device to deliver a vapor, a cloud, or an aerosol comprising scent media of FIG. 7A, according to at least one illustrated embodiment.
Figure 7F:
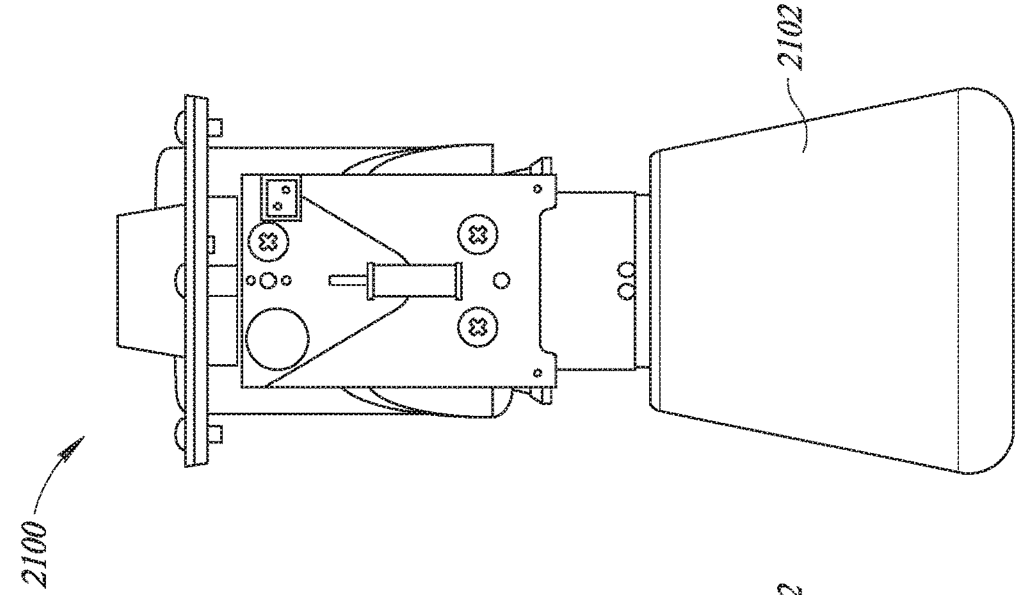
FIG. 7F is another side view of components of the delivery device to deliver a vapor, a cloud, or an aerosol comprising scent media of FIGS. 21A-21D, according to at least one illustrated embodiment.
Figure 7E:
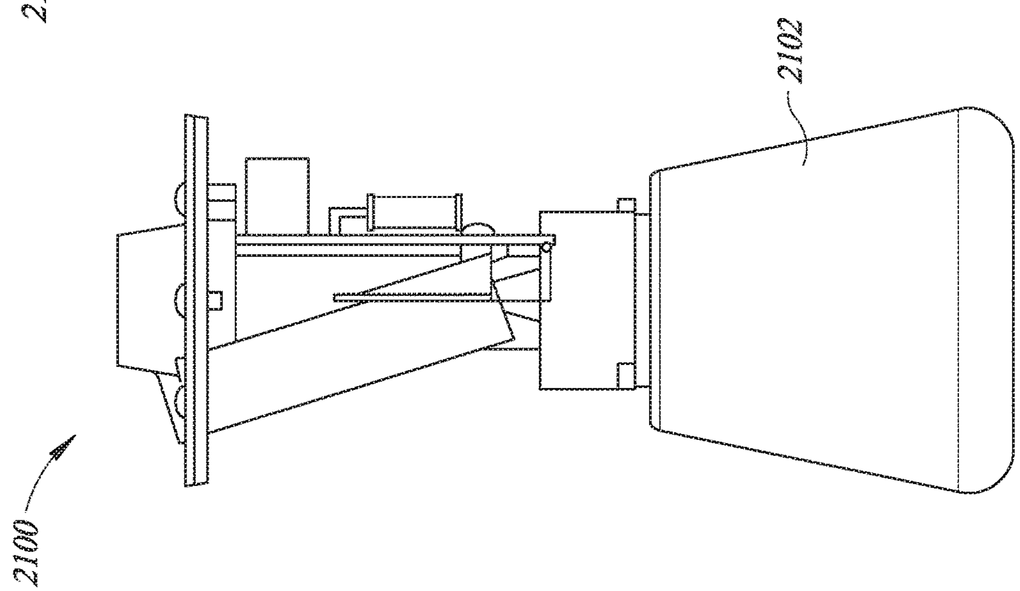
FIG. 7E is a side view of components of the delivery device to deliver a vapor, a cloud, or an aerosol comprising scent media of FIGS. 7A-7D, according to at least one illustrated embodiment.
Figure 7D:
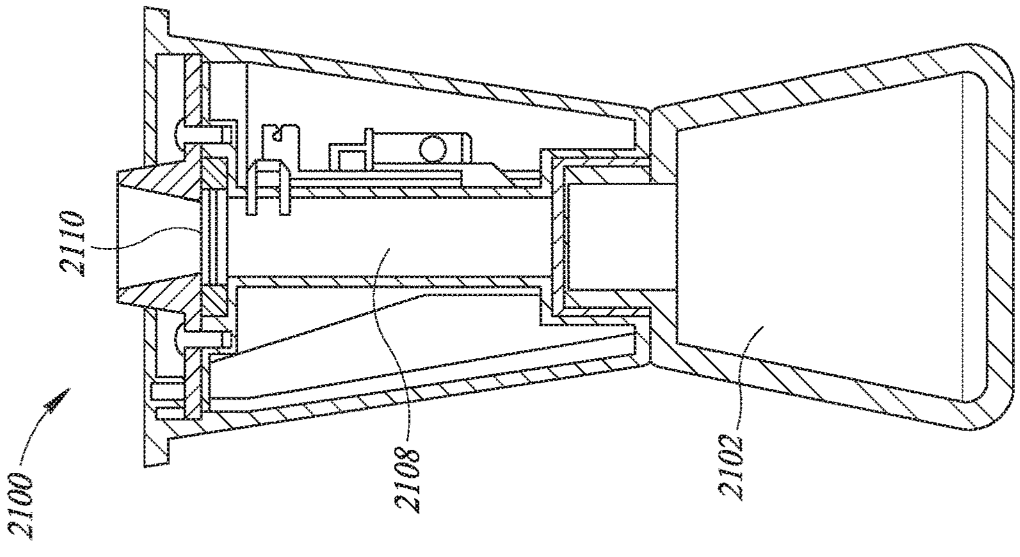
FIG. 7D is a cross-sectional side view of the delivery device to deliver a vapor, a cloud, or an aerosol comprising scent media of FIGS. 7A-7C, according to at least one illustrated embodiment.

FIGS. 7B, 7C, and 7D illustrate perspective, side, and cross-sectional side views, respectively, of the delivery device 2100. FIGS. 7E and 7F illustrate two different side views of the delivery device 2100 with the housing of the main body 2104 removed to reveal internal components of the main body 2104.

Figure 8B:
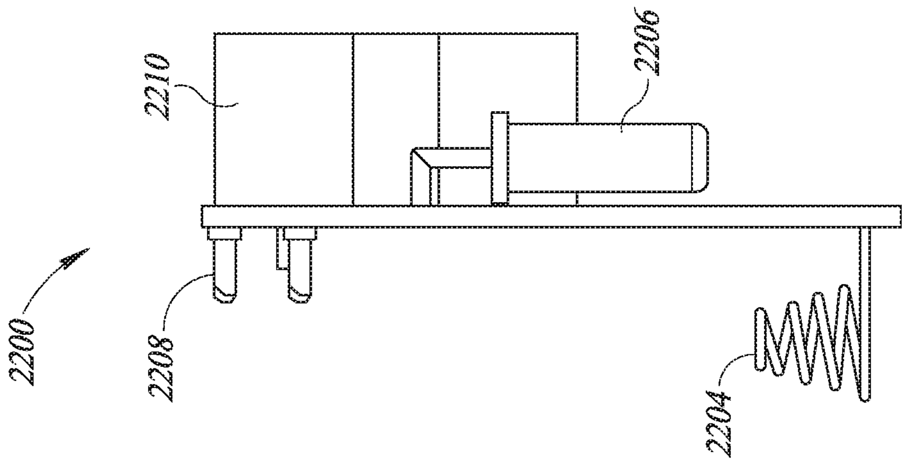
FIG. 8B is a side view of the printed circuit board and associated components of FIG. 8A, according to at least one illustrated embodiment.
Figure 8A:
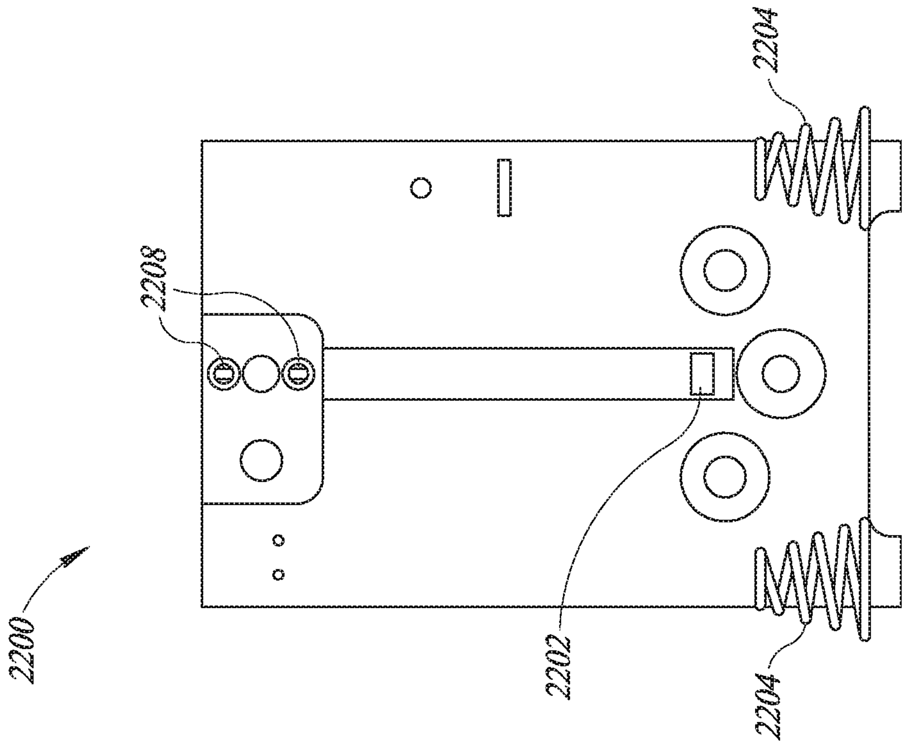
FIG. 8A is a rear view of a printed circuit board and associated components coupled thereto for use in the delivery device to deliver a vapor, a cloud, or an aerosol comprising scent media of FIGS. 7A-7F, according to at least one illustrated embodiment.

FIGS. 8A-8D illustrate the printed circuit board 2200 of the delivery device 2100 with associated components coupled thereto. FIG. 8A is a rear view of the printed circuit board 2200 and illustrates that the printed circuit board 2200 includes an LED 2202 physically and electrically coupled to the rear surface thereof, which can be operable to light up or turn on when the delivery device 2100 is generating a cloud of vaporized scent media or scent media in aerosol form, and to turn off when the delivery device 2100 is not generating a cloud of vaporized scent media or scent media in aerosol form. The LED can be useful to a user of the device 2100 because when the LED lights up, the user can be confident that power is being supplied to the printed circuit board 2200. FIG. 22A also illustrates that the rear surface of the printed circuit board 2200 is physically and electrically coupled to two metallic springs 2204, each of which is positioned and configured to act as a contact for, and to partially support or cradle, one of the batteries 2106. One of the springs 2204 can act as a positive contact, while the other of the springs 2204 can act as a negative contact, for the batteries 2106, such that the batteries 2016 will be installed within the device 2100 with their polarities reversed with respect to one another.

Figure 8D:
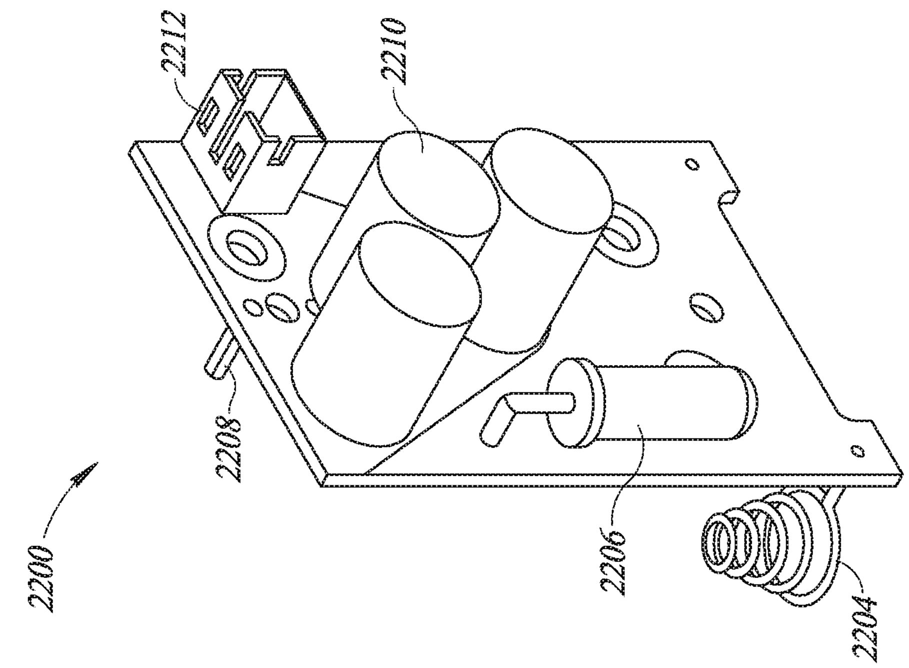
FIG. 8D is a perspective view of the printed circuit board and associated components of FIGS. 8A-8C, according to at least one illustrated embodiment.
Figure 8C:
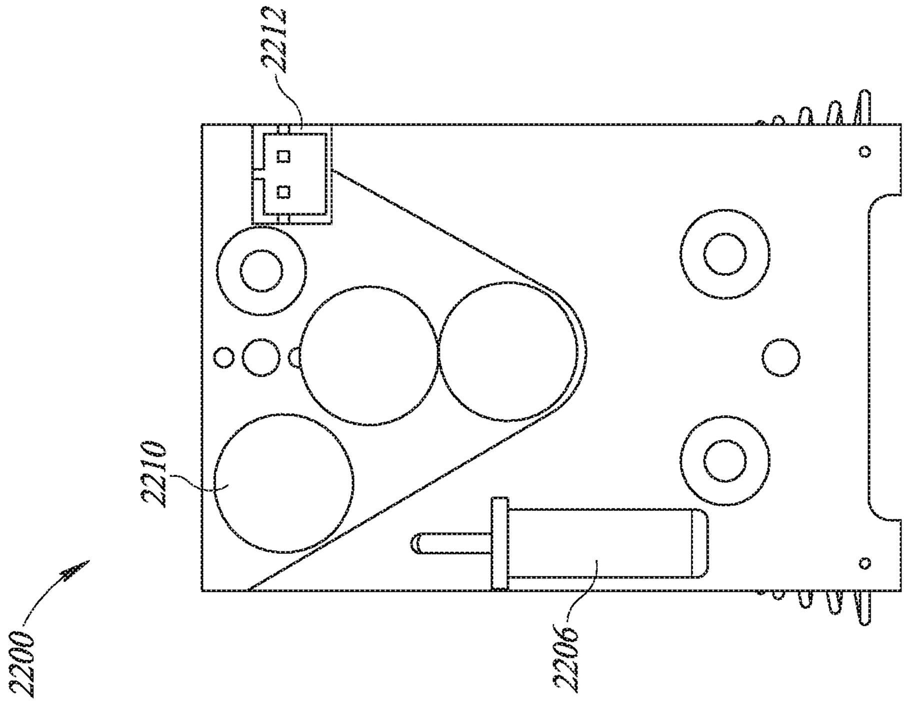
FIG. 8C is a front view of the printed circuit board and associated components of FIGS. 8A and 8B, according to at least one illustrated embodiment.
Figure 8F:
FIG. 8F is a side view of the printed circuit board of FIGS. 8A-8D, without the associated components coupled thereto of FIGS. 8A-8D, according to at least one illustrated embodiment.
Figure 8E:
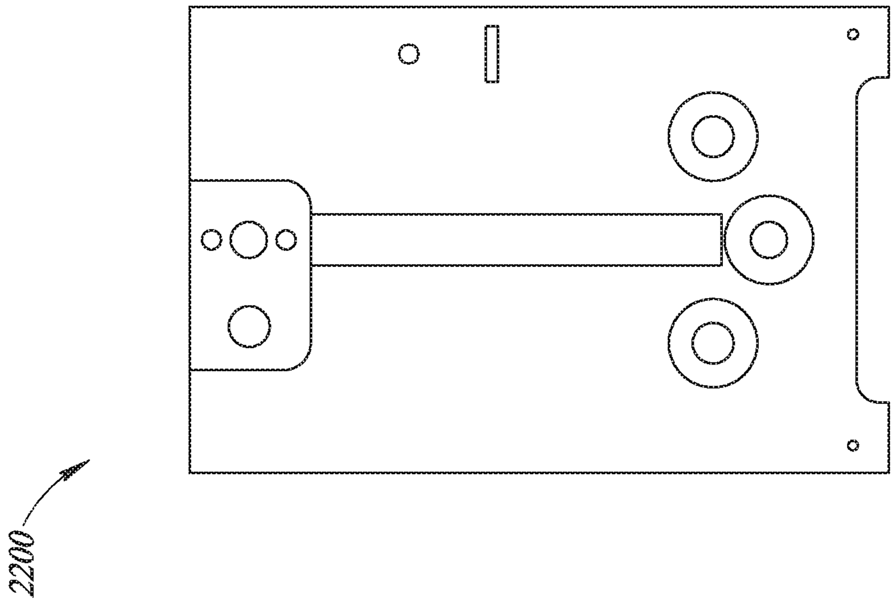
FIG. 8E is a rear view of the printed circuit board of FIGS. 8A-8D, without the associated components coupled thereto of FIGS. 8A-8D, according to at least one illustrated embodiment.
Figure 8H:
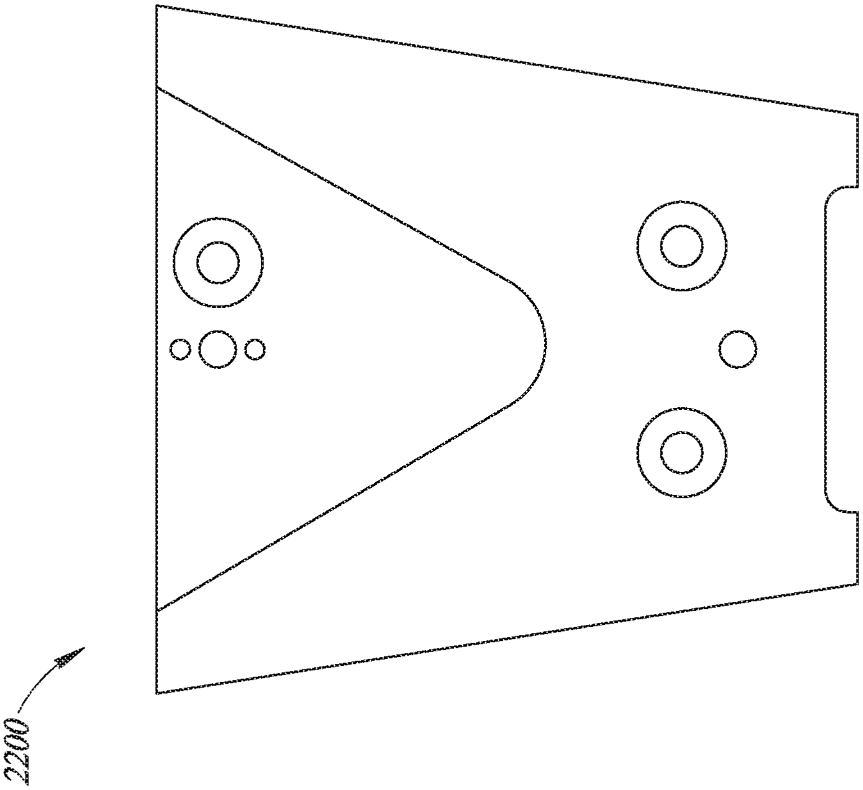
FIG. 8H is a front view of an alternative configuration of the printed circuit board of FIGS. 8A-8D, without the associated components coupled thereto of FIGS. 8A-8D, according to at least one illustrated embodiment.
Figure 8G:
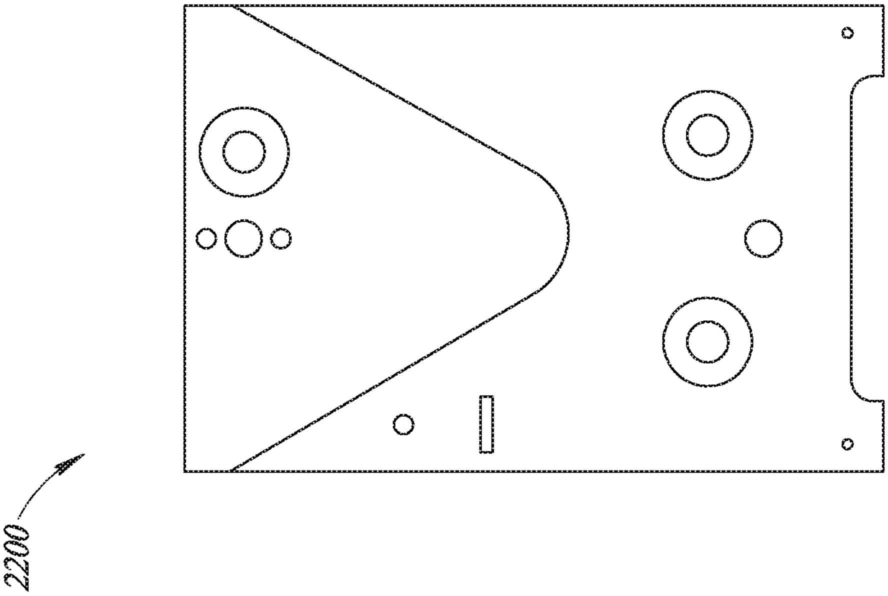
FIG. 8G is a front view of the printed circuit board of FIGS. 8A-8D, without the associated components coupled thereto of FIGS. 8A-8D, according to at least one illustrated embodiment.

FIG. 8B is a side view of the printed circuit board 2200 and illustrates that the rear surface of the printed circuit board 2200 is also physically and electrically coupled to a plurality of gold pins 2208 to which a fluid sensor can be physically and electrically coupled. FIG. 8C is a front view of the printed circuit board 2200 and illustrates that the front surface of the printed circuit board 2200 can include an electrical connector 2212, which can be a JST connector, to allow an operator to physically and electrically couple other electronic devices, such as the piezo-electric device 2110, to the printed circuit board 2200 and to allow the printed circuit board and other associated components coupled thereto to communicate with (e.g., transmit signals to or receive signals from) such other electronic devices including the piezo-electric device 2110. FIG. 8C also illustrates that the front surface of the printed circuit board 2200 is physically and electrically coupled to a tilt sensor 2206, which can include an accelerometer or a ball tilt switch in which a ball moves and connects pins to complete an electrical circuit when the device 2100 is tilted, and to a plurality of capacitors 2210 for storing electrical energy. FIG. 8D is a perspective view of the printed circuit board 2200 and illustrates a perspective view of the printed circuit board 2200 with the associated components coupled thereto. FIGS. 8E-8G illustrate the printed circuit board 2200 without the associated components coupled thereto.

As illustrated in FIGS. 7A-7F, the rear of the printed circuit board 2200, illustrated directly in FIG. 8A, faces toward the conduit 2108 and the center of the delivery device 2100, while the front of the printed circuit board 2200, illustrated directly in FIG. 8C, faces away from the conduit 2108 and the center of the delivery device 2100. In some implementations, the printed circuit board 2200 receives power from a source at between 2.0 and 3.4 Volts DC, and provides power to a load at 140 KHz and at 65 Volts peak-to-peak. FIG. 8H illustrates a front view of an alternative shape and configuration for the printed circuit board 2200. FIGS. 8A-8H illustrate some examples of possible dimensions of the printed circuit board 22, with the numbers used in millimeters. It will be understood that the specific dimensions provided in these Figures are merely examples of possible suitable dimensions.

To operate the delivery device 2100, a user can fill the base 2102 with scent media in a liquid form and assemble the device 2100 except for the batteries 2106 and the external cover 2114, such as by screwing or threading the base 2102 onto the main body 2104. The user can then insert the batteries 2106 into the device 2100 through the apertures 2122 in the internal cover 2112, such that the batteries are partially cradled by the recesses of the flanges 2118, and such that bottom terminals of the batteries 2106 are in electrical contact with the springs 2204. The user can then couple the external cover 2114 to the rest of the device 2100, such as by threading or press-fitting the external cover into a top end of the main body 2104. An underside of the external cover 2114 can include a strip of electrically-conductive material, such as metal, which can engage the top terminals of the batteries 2106 and electrically couple the upper terminal of one of the batteries 2106 to the upper terminal of the other one of the batteries 2106.

The user can then lift and tilt the device 2100, such that the fluid flows, under the force of gravity, from the base 2102, through the conduit 2108, to the piezo-electric device 2110. Once the user tilts the device 2100, for example to dock with the primary vessel, the tilt sensor 2206 can generate and transmit a signal indicating that the device 2100 has been tilted. Further, once the fluid flows to the piezo-electric device 2110, the fluid may come into contact with a fluid sensor coupled to the pins 2208 and generate and transmit a signal indicating that the fluid has reached the fluid sensor. Further still, the device 2100 can include a pressure-sensitive switch on a bottom surface thereof which, when the device 2100 is picked up off of a flat surface, can generate and transmit a signal that the device 2100 has been picked up. In some implementations, the device 2100 includes no manually-operated switches or buttons, and receives no input from the user, other than one, two, or three of the signals described above.

Upon receipt of any one, any two, or all three of such signals, the device 2100 can activate the piezo-electric device 2110 to begin generating a cloud of vaporized scent media or scent media in aerosol form from the scent media in liquid form. Because the device 2100 is tilted sideways or upside-down, the cloud of vaporized scent media or scent media in aerosol form can flow out of the device 2100 through the hollow cone-shaped portion 2120, and can be consumed directly by the user or can be poured into another container or vessel for subsequent consumption. In some implementations, the device 2100 includes an internal timer and automatically turns off or de-activates the piezo-electric device 2110 to stop generating the cloud of vaporized scent media or scent media in aerosol form after a time period of about 5, about 10, about 15, or about 20 seconds. In other implementations, the device 2100 continues to operate and generate the vaporized scent media or scent media in aerosol form until the device 2100 is once again oriented upright or placed back on a flat horizontal surface.

When the fluid within the base 2102 runs out, the user can unscrew or unthread of the base 2102 from the main body 2104 of the device 2100, refill the base 2102 with more of a desired scent media in a fluid form, screw or thread the base 2102 back on to the main body 2104, and then resume using the device 100. When the batteries 2106 die, no longer power the device 2100, and need to be replaced, the user can remove the external cover 2114 from the rest of the device 2100, such as by unscrewing, unthreading, or turning the external cover 2114 with respect to the rest of the device 2100. The old batteries 2106 within the device 100 can then be removed and new batteries 2106 can be installed in their place. The user can then re-install the external cover 2114 onto the rest of the device 2100 and resume using the device 2100.

In some implementations, the external cover 2114, or a surface of the rest of the device 2100 that engages with the external cover 2114, includes a detent, and the detent is engaged as the external cover 2114 is turned with respect to the rest of the device 2100 just before the external cover 2114 is released from the rest of the device 2100. Engagement of the detent can serve as a signal to the user that the external cover 2114 is about to be released from the rest of the device 2100. Once the user releases and removes the external cover 2114 from the rest of the device 2100, the batteries are disconnected and the device is unable to operate. Thus, the external cover 2114 can act as a switch, where removing the external cover 2114 from the rest of the device 2100 switches the device 2100 off and engagement of the external cover 2114 with the rest of the device 2100 switches the device 2100 on.

Figure 9:
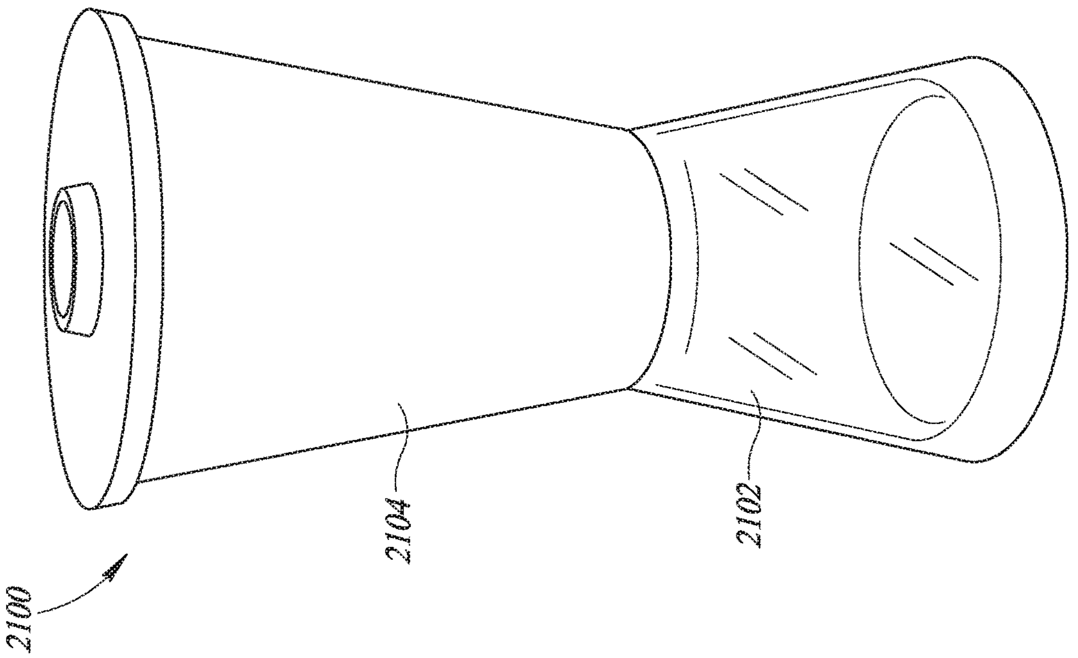
FIG. 9 is a three-dimensional rendering in a perspective view of the delivery device to deliver a vapor, a cloud, or an aerosol comprising scent media of FIGS. 7A-7F, according to at least one illustrated embodiment.

FIG. 9 illustrates a three-dimensional rendering of the device 2100, showing its overall shape. In particular, the base 2102 of the device 2100 has a geometric shape including a truncated cone, and the main body 2104 of the device 2100 has a geometric shape including an inverted truncated cone, such that the device 2100 has an overall geometric shape resembling an hourglass, with a bottom portion that is smaller than its top portion.

Figure 10:
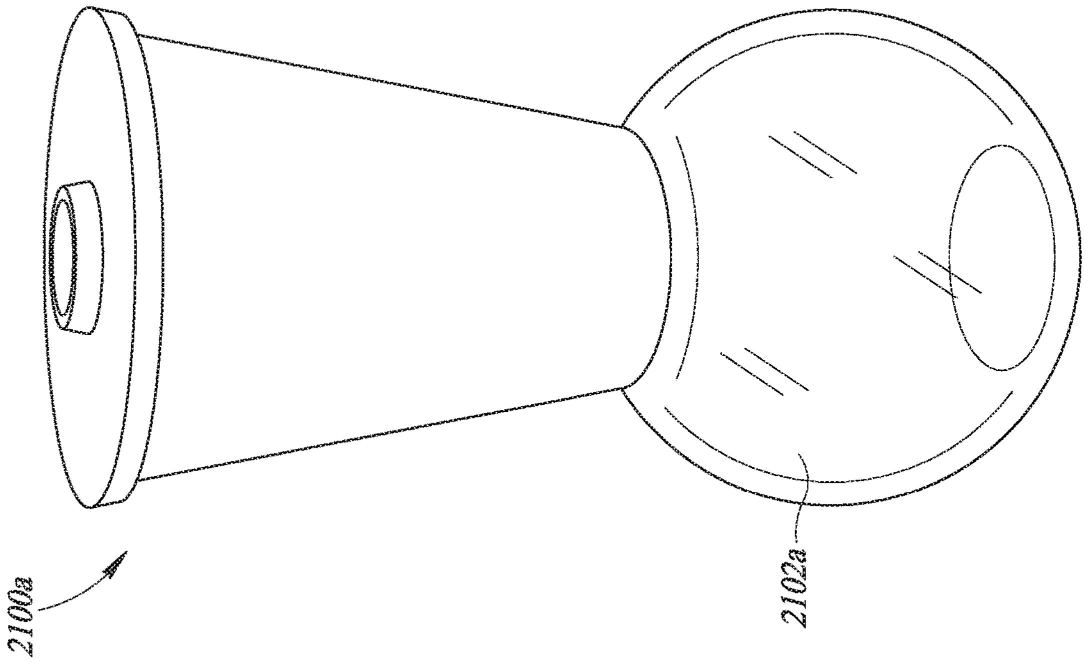
FIG. 10 is a three-dimensional rendering in a perspective view of an alternative configuration for the delivery device to deliver a vapor, a cloud, or an aerosol comprising media, according to at least one illustrated embodiment.

FIG. 10 illustrates one alternative implementation of the device 2100*a*, in which the base 2102*a* has a geometric shape including a sphere with a truncated bottom end and a truncated top end.

Figure 11:
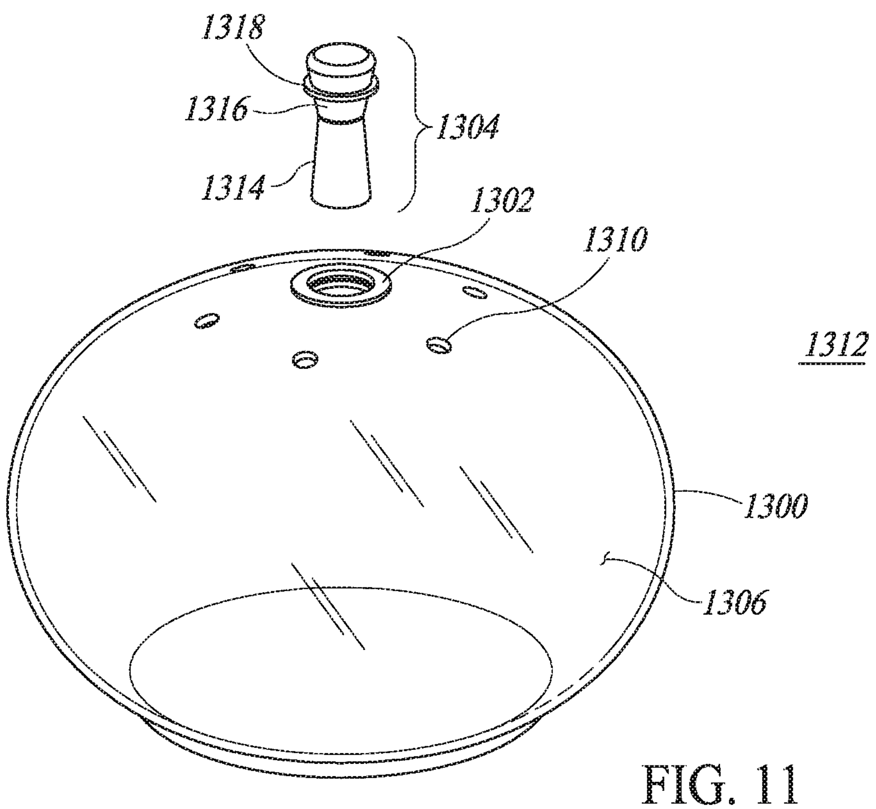
FIG. 11 is an isometric view of a primary vessel and a dock for use with at least one distinct delivery device selectively dockable to the primary vessel via the dock and operable to dispense an aerosol into an interior of the primary vessel for ingestion by a person or other animal, according to at least one illustrated implementation.
Figure 12:
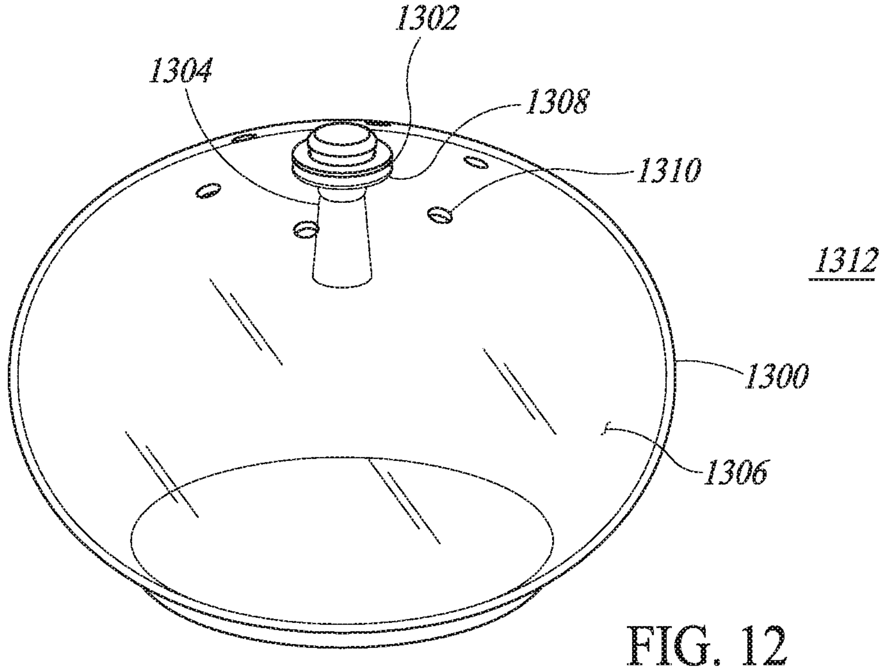
FIG. 12 is an isometric view of the primary vessel of FIG. 11 with the distinct delivery device removably docked thereto via the dock, the primary vessel and distinct delivery device in a first orientation in which the distinct delivery device does not dispense an aerosol into the interior of the primary vessel.
Figure 13:
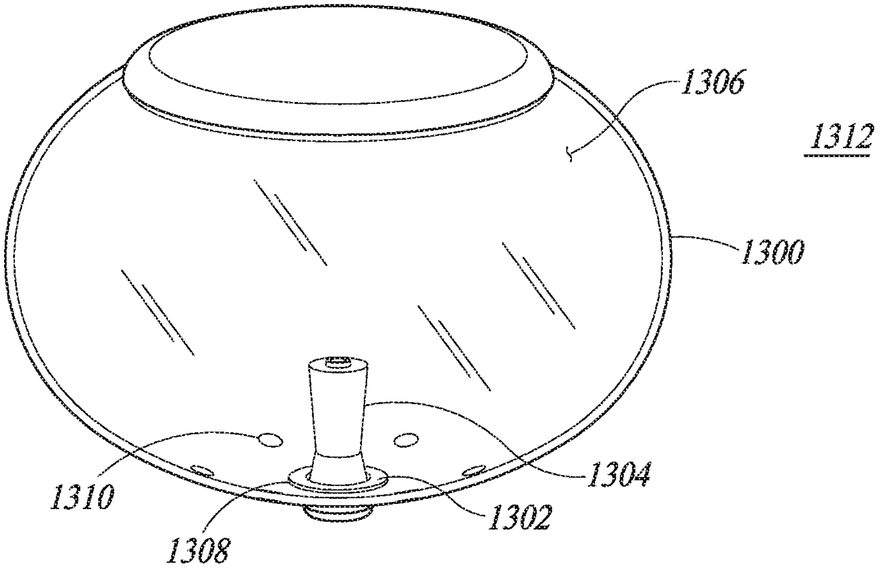
FIG. 13 is an isometric view of the primary vessel with the distinct delivery device removably docked thereto of FIG. 12, the primary vessel and distinct delivery device in a second orientation in which the distinct delivery device dispenses an aerosol into the interior of the primary vessel.

FIGS. 11, 12 and 13 illustrate a primary vessel 1300 and optional dock 1302 for use with at least one distinct delivery device 1304 removably dockable to the primary vessel 1300 via the dock 1302 and operable to dispense an aerosol into an interior 1306 of the primary vessel 1300 for ingestion by a person or other animal, according to at least one illustrated implementation. In particular, FIG. 11 shows the primary vessel 1300 and dock 1302 without the distinct delivery device 1304 docked thereto. FIG. 12 shows the primary vessel 1300 with the distinct delivery device 1304 removably docked thereto, the primary vessel 1300 and distinct delivery device 1304 in a first orientation (e.g., right side up or upside up) in which the distinct delivery device 1304 does not dispense an aerosol into the interior 1306 of the primary vessel 1300. FIG. 13 shows the primary vessel 1300 with the distinct delivery device 1304 removably docked thereto, the primary vessel 1300 and distinct delivery device 1304 in a second orientation (e.g., upside down) in which the distinct delivery device 1304 dispenses an aerosol into the interior 1306 of the primary vessel 1300.

The primary vessel 1300 may be similar, in some aspects to the primary vessel illustrated in FIG. 1, although may omit a neck, and may have an aperture 1308 and optional dock 1302 to allow docking of the distinct delivery device 1304. The aperture 1308 and dock 1302 may be located centrally, thus may be denominated as a central aperture and central dock, although such positioning is not required. The aperture 1308 and optional dock 1302 are sized to removable receive, and preferably detachably secure a distinct delivery device 1304 (e.g., a nebulizer).

The primary vessel 1300 includes one or more vents or outlet ports 1310 (only one called out) that provide fluid communications between the interior 1306 and an exterior 1312. The vent(s) or outlet port(s) 1310 may, for example, be arrayed around the aperture 1308. The vent(s) or outlet port(s) 1310 allow at least some of aerosol to transit to the exterior 1312 from the interior 1306 of the primary vessel 1300 after being dispensed by the distinct delivery device 1304.

The optional dock may take the form of a gasket, identical or similar to the annular gaskets 138 best illustrated in FIGS. 2, 3 and 4.

Notably, the distinct delivery device 1304, particularly the exterior thereof, may be modified from that illustrated in FIGS. 1, 7A-7F, 9 and 10. In particular, since the distinct delivery device 1304 docks via the aperture 1308 and/or dock 1302, a widest part of an upper portion 1314 (e.g., portion in which outlet or nozzle is located) of the distinct delivery device 1304 is sized to fit through the aperture 1308 and/or dock 1302. A part of lower portion 1316 (e.g., portion in away from outlet or nozzle is located) is sized to engage the aperture 1308 and/or dock 1302. Thus, widest part of an upper portion 1314 is more narrow that a part of the lower portion 1316 that engages an edge of the aperture 1308 and/or dock 1302. That also means that the radially outwardly extending lip, edge or plate, for example seen FIGS. 7A-7F, 9 and 10, would not extend radially outward from a top of the distinct delivery device 1304. Instead, a peripheral lip, edge or plate 1318 may extend radially outward from the lower portion body of the distinct delivery device 1304, at a location along the distinct delivery device 1304 that engages the aperture 1308 and/or dock 1302. The peripheral lip, edge or plate 1318 may be sized to be removably or detachably securingly received by an inner channel of the dock 1302 (e.g., a gasket). The fit between the dock 1302 and the peripheral lip, edge or plate 1318 may be a tight fit or interference fit.

The distinct delivery device 1304 dispenses the aerosol toward a bottom of the primary vessel 1300, (the bottom illustrated as e.g., a flat portion at lower portion of the primary vessel 1300 in FIGS. 11 and 12, and at upper portion of the inverted primary vessel 1300 in FIG. 13), for example along an axis that extends perpendicularly from the bottom, or within approximate 12 degrees of such an axis.

The distinct delivery device 1304 may include one or more sensors that are responsive to orientation, for example one or more single axis or multi-axis accelerometers or other orientation sensors. The sensors may be responsive to an orientation of the distinct delivery device 1304, causing the distinct delivery device 1304 to produce and dispense aerosol when in an inverted orientation (e.g., as shown in FIG. 13) and to stop dispensing aerosol when in an un-inverted orientation (e.g., as shown in FIG. 12). Thus, in response to being inverted, the distinct delivery device 1304 generates and dispenses aerosol into the interior of the primary vessel 1300, and aerosol then wafts from the interior out to the exterior via vents or outlet ports 1310.

In some implementations, the scent media used in any one of the delivery devices described herein can include functional additives or active agents, in some cases for therapeutic applications, such as vitamins, minerals, supplements, other nutrients to provide nutrition, or drugs, medications, or pharmaceutical agents. As specific examples, such compounds can be used to assist a user in recovering from addictions such as opiate or food addictions, or to assist a user in controlling their metabolism. In some cases, such compounds can be provided in a liquid, and either a concentrated or a purified form, and can be vaporized or aerosolized by one of the delivery devices described herein and poured over a food or a beverage that either does not contain such compounds or that contains such compounds in a much lower concentration than the vapor or aerosol.

One embodiment provides a composition for ortho-nasal and retro-nasal food or therapeutic applications, the composition comprising at least one TRPV agonist or agonists (or antagonists) and a sufficient amount of water/alcohol mix to aerosolize the composition, wherein a total concentration of all TRPV agonists is in the range of 50 micrograms/ml-500 mg/ml.

In various specific embodiments, the one or more receptor protein agonist compositions may include: sodium iodide, sodium chloride, magnesium chloride, capsaicin, piperine, ground cinnamon, a cannabinoid, pimento, onion, clove, thyme, ginger, menthol, or TRPV antagonists, and chocolate, Irish cream, caramel, lemon, lime, mango, raspberry, watermelon, blueberry, strawberry, mint, popcorn, meat, or nicotine.

The aerosolized composition may be delivered by smelling a cloud suspended in the air or in the process of eating or drinking. For example, the aerosolized composition may be generated in the air before the nose, or above the top surface of a beverage or foodstuff immediately before consumption. The cloud of droplets are capable of accessing oropharynx by smelling the cloud or during the act of ingestion.

Another embodiment provides a method of administering the composition disclosed herein in for ortho-nasal or retro-nasal food or therapeutic applications, the method comprising: attaching a vial or cartridge containing the composition to a nutrition cloud generator or nebulizer; generating a cloud of droplets in the air or over a surface of a foodstuff for some duration of time ranging from about 1 second to as much as 30 minutes; and smelling the cloud of droplets or ingesting the foodstuff while the cloud of droplets is suspended over the foodstuff, thus bringing the cloud of droplets into the oropharynx.

In some embodiments, the foodstuff is a beverage, such as water, soda or cocktail.

In other embodiments, the foodstuff is solid food such as bread, rice, pasta, and the like.

Various examples of the compositions are described herein in more detail.

Salts with Lime or Mango

Begin with a vial of water 25 milliliters. Add 25 milligrams to 3 grams ground salt (including one or all of sodium iodide, sodium chloride, magnesium chloride), and 10 milliliters of lime or mango juice. Attach the vial to a nutrition cloud generator or nebulizer, as in the Nimbus device. Tip the Nimbus before a nose, or over a glass of water, soda or cocktail that does not have a noticeable quantity of salt or mango/lime. A cloud of salty lime or mango droplets forms in the air before the nose or over the beverage with a duration of cloud production of up to 10 seconds. Smell the cloud or drink the beverage with the cloud of salty lime or salty mango over the drink. The act of smelling or of drinking brings the cloud of salty droplets into the oropharynx and produces a powerful sensation of saltiness and flavor, and in the case of the beverage the impression that the flavor of lime or mango belongs to the drink itself. It is as if one has consumed a beverage that contains salt and the taste of lime or mango. Sensations of taste and olfaction combine to produce this powerful effect; and since the mass of cloud dispersed over the glass is less than 1 milligram total mass, the total quantity of salt is less than approximately 10 micrograms.

Pepper or Pepper with Lemon

Begin with a vial of water 25 milliliters. Add 25 milligrams to 3 grams ground pepper (black pepper containing the active ingredient piperine), and optionally 10 milliliters of lemon juice. Attach the vial to a nutrition cloud generator, as in the Nimbus device. Tip the Nimbus before a nose, or over a glass of water, soda or cocktail that does not have a noticeable quantity of pepper or lemon. A cloud of pepper or possibly lemon pepper droplets forms in the air before the nose or over the beverage with a duration of production of up to 10 seconds. Smell the cloud or drink the beverage with the cloud of pepper over the drink. The act of smelling or drinking brings the cloud of pepper droplets into the oropharynx and produces a powerful sensation of pepper and the impression, in the case of the beverage, that the flavor of pepper or lemon pepper belongs to the drink itself. It is as if one has consumed a beverage that contains pepper or lemon pepper. Sensations of taste and olfaction couple in this case with the sensation of heat delivered by piperine acting on the TRPV1 protein to produce this powerful effect; and since the mass of cloud dispersed over the glass is less than 1 milligram total mass, the total quantity of pepper is less than approximately 10 micrograms.

Cinnamon or Cinnamon with Chocolate

Begin with a vial of water 25 milliliters. Add 25 milligrams to 3 grams ground cinnamon and optionally add 10 milliliters of chocolate flavored water. Attach the vial to a nutrition cloud generator, as in the Nimbus device. Tip the Nimbus before a nose, or over a glass of water, soda or cocktail that does not have a noticeable quantity of cinnamon or cinnamon/chocolate. A cloud of cinnamon droplets forms before the nose or over the beverage with a duration of production of up to 10 seconds. Smell the cloud or drink the beverage with the cloud of cinnamon over the drink. The act of smelling or drinking brings the cloud of cinnamon droplets into the oropharynx and produces a powerful sensation of cinnamon and, in the case of the beverage, the impression that the flavor of cinnamon belongs to the drink itself. It is as if one has consumed a beverage that contains cinnamon and possibly chocolate. Sensations of taste and olfaction combine with the warmth sensation delivered by cinnamon acting on heat sensation proteins (i.e. TRPV3 and TRPV4) to produce this powerful effect; and since the mass of cloud dispersed over the glass is less than 1 milligram total mass, the total quantity of cinnamon is less than approximately 10 micrograms.

Ginger or Ginger with Tea

Begin with a vial of water 25 milliliters. Add 25 milligrams to 3 grams ground ginger and optionally add 10 milliliters of tea. Attach the vial to a nutrition cloud generator, as in the Nimbus device. Tip the Nimbus before a nose, or over a glass of water, soda or cocktail that does not have a noticeable quantity of ginger. A cloud of ginger droplets forms before the nose or over the beverage with a duration of production of up to 10 seconds. Smell the cloud or drink the beverage with the cloud of ginger over the drink. The act of smelling or drinking brings the cloud of ginger droplets into the oropharynx and, in the case of the beverage, produces a powerful sensation of ginger and the impression that the flavor of ginger belongs to the drink itself. It is as if one has consumed a beverage that contains ginger and possibly tea. Sensations of taste and olfaction combine with the warmth sensation delivered by ginger acting on heat sensation proteins (i.e. TRPV3 and TRPV4) to produce this powerful effect; and since the mass of cloud dispersed over the glass is less than 1 milligram total mass, the total quantity of ginger is less than approximately 10 micrograms.

Menthol with Mint or Mango

Begin with a vial of 40% Vodka 25 milliliters. Add 25 milligrams to 3 grams ground menthol crystals, and 10 milliliters of mint-leaf or mango flavored water. Attach the vial to a nutrition cloud generator or nebulizer, as in the Nimbus device. Tip the Nimbus before a nose o over a glass of water, soda or cocktail that does not have a noticeable quantity of menthol or mint or mango. A cloud of menthol droplets forms before the nose or over the beverage with a duration of production of up to 10 seconds. Smell the cloud or drink the beverage with the cloud of menthol over the drink. The act of smelling or drinking brings the cloud of menthol droplets into the oropharynx and produces a powerful sensation of coldness (delivered by the action of menthol on the TRPV8 membrane protein) and, in the case of the drink, the impression that the flavor of menthol belongs to the drink itself. It is as if one has consumed a beverage that contains menthol and possibly the taste of mint or mango. Sensations of taste and olfaction combine to produce this powerful effect; and since the mass of cloud dispersed over the glass is less than 1 milligram total mass, the total quantity of menthol is less than approximately 10 micrograms.

Resolvin D2

Begin with a vial of water 25 milliliters. Add 50 micrograms of Resolvin D2 (7S,16R,17S-trihydroxy-DHA), and 10 milliliters of mint-leaf flavored water. Attach the vial to a nutrition cloud generator or nebulizer, as in the Nimbus device. Tip the Nimbus before a nose, or over a glass of water, soda or other beverage, directly into the mouth or nose, or optionally into a holding chamber (i.e. spacer) into which the cloud collects. A cloud of Resolvin D2 forms before the nose, or in the oropharynx, with duration of production ranging from one second to up to 30 minutes. The act of smelling or inhaling brings the cloud of mint-flavored Resolvin D2 droplets into the oropharynx and possibly into the airways and, by virtue of the TRPV antagonist nature of Resolvin D2, potentially reduces cough reflex while also producing a satisfying flavor of mint.

Essential Oil, Fragrance Oil, and Flavor Extract Compositions

Begin with a vial of water 25 milliliters. Add 0.5 to 1 milliliter of essential oil, fragrance oil or flavor extract, as in cacao oil, caramel oil, cinnamon bark oil, coffee oil, eucalyptus oil, palm oil, fig oil, grapefruit oil, hazelnut oil, honeydew melon oil, lavender or spike lavender oil, lemongrass oil, lime oil, black or green pepper oil, peppermint oil, rosemary oil, strawberry oil, smoke oil, tobacco vanilla oil, vanilla oil, chocolate extract, anise extract Attach the vial to a nutrition cloud generator, as in the Nimbus device. Tip the Nimbus before a nose, or over a glass of water, soda or cocktail that does not have a noticeable quantity of the oil or extract. A cloud of flavored droplets forms before the nose or over the beverage with a duration of production of up to 10 seconds. Smell the cloud or drink the beverage with the cloud of flavor over the drink. The act of smelling or drinking brings the cloud of droplets into the nasopharynx and, in the case of the beverage, produces a powerful sensation of the flavor and the impression that the flavor belongs to the drink itself. It is as if one has consumed a beverage that contains the flavor. Sensations of taste and olfaction possibly combine with the warmth sensation delivered by, e.g., the pepper acting on heat sensation proteins (i.e., TRPV1 in the case of pepper) to produce this powerful effect; and since the mass of cloud dispersed over the glass is less than 1 milligram total mass, the total quantity of ginger is less than approximately 10 micrograms.

Aspects

Aspect 1. A composition for ortho-nasal or retro-nasal food or therapeutic applications, the composition comprising:

agonists or antagonists of at least one type of transient receptor potential vanilloid (TRPV) receptor, and a sufficient amount of water or a mixture of water and alcohol to aerosolize the composition in a form of droplets less than 100 microns in size which carry the agonists or antagonists, wherein the concentration of all agonists or antagonists in the composition is in a range of 50 micrograms/milliliters to 2 milligrams/milliliter, the composition to be delivered ortho-nasally and/or retro-nasally as an aerosol.

Aspect 2. The composition of aspect 1 wherein the agonists or antagonists of are agonists or antagonists at least one of TRPV1 receptors, TRPV3 receptors, TRPV4 receptors, or TRPV8 receptors.

Aspect 3. The composition of aspect 1 wherein the composition includes two or more types of TRPV antagonists.

Aspect 4. The composition of aspect 1 wherein the composition further includes agonists or antagonists of one or both of olfactory receptors or taste receptors.

Aspect 5. The composition of aspect 1 wherein the composition includes agonists or antagonists of all: at least one type of TRPV receptors, olfactory receptors, and taste receptors.

Aspect 6. The composition of aspect 1 wherein the composition includes one or more of the following: sodium iodide, sodium chloride, magnesium chloride, capsaicin, and pipeline.

Aspect 7. The composition of aspect 1 wherein the composition includes one or more of the following: ground cinnamon, a cannabinoid, pimento, onion, clove, thyme, ginger, menthol, Irish cream, lemon, lime, mango, raspberry, watermelon, blueberry, strawberry, popcorn, meat, Resolvin D2 or nicotine.

Aspect 8. The composition of aspect 1 wherein the composition includes linalool.

Aspect 9. The composition of aspect 1 wherein, in the aerosolized form the droplets have a median droplet size of less than 20 microns.

Aspect 10. The composition of aspect 1 wherein, in the aerosolized form the droplets are between 6 microns and 10 microns in size.

Aspect 11. The composition of aspect 1, wherein, in the aerosolized form, at least a majority of the droplets are between 5 microns and 10 microns in size.

Aspect 12. The composition of aspect 1 wherein a mass of the composition as delivered to a nose in aerosolized form is less than 1 milligram total mass, and a total quantity of substances acting on TRPV, olfactory, or taste receptors is less than approximately 100 micrograms.

Aspect 13. The composition of aspect 12 wherein the composition is contained in a single or multiple dose disposable cartridge.

Aspect 14. The composition of any of aspects 1 through 13 wherein the concentration of all agonists or antagonists of taste, olfactory and TRPV receptors is in a range of 50 micrograms/milliliters to 1 milligrams/milliliter.

Aspect 15. The composition of any of aspects 1 through 11 wherein the concentration of all agonists or antagonists of TRPV, olfactory, or taste receptors is in a range of 50 micrograms/milliliters to 500 micrograms/milliliters.

Aspect 16. A method of administering a composition for ortho-nasal or retro-nasal therapeutic applications, method comprising:

generating an aerosol of a cloud of droplets with agonists or antagonists of at least one type of transient receptor potential vanilloid (TRPV) receptor, the aerosol in a form of droplets less than 100 microns in size which carry the agonists or antagonists, wherein the concentration of all agonists or antagonists in the composition is in a range of 50 micrograms/milliliters to 2 milligrams/milliliter; and providing the aerosol in an space from which the aerosol is imbibeable either ortho-nasally or retro-nasally.

Aspect 17. The method of aspect 16 wherein generating an aerosol of a cloud of droplets includes generating an aerosol of a cloud of droplets where the agonists or antagonists are agonists or antagonists of at least one of TRPV1 receptors, TRPV3 receptors, TRPV4 receptors, or TRPV8 receptors.

Aspect 18. The method of aspect 16 wherein generating an aerosol of a cloud of droplets includes generating an aerosol of a cloud of droplets where the agonists or antagonists are agonists or antagonists of two or more types of TRPV antagonists.

Aspect 19. The method of aspect 16 wherein generating an aerosol of a cloud of droplets includes generating an aerosol of a cloud of droplets with agonists or antagonists of one or both of olfactory receptors or taste receptors.

Aspect 20. The method of aspect 16 wherein generating an aerosol of a cloud of droplets includes generating an aerosol of a cloud of droplets with agonists or antagonists of all of: at least one type of TRPV receptors, olfactory receptors, and taste receptors.

Aspect 21. The method of aspect 16 wherein generating an aerosol of a cloud of droplets includes generating an aerosol of a cloud of droplets with one or more of the following: sodium iodide, sodium chloride, magnesium chloride, capsaicin, and piperine.

Aspect 22. The method of aspect 16 wherein generating an aerosol of a cloud of droplets includes generating an aerosol of a cloud of droplets with one or more of the following: ground cinnamon, a cannabinoid, pimento, onion, clove, thyme, ginger, menthol, Irish cream, lemon, lime, mango, raspberry, watermelon, blueberry, strawberry, popcorn, meat, Resolvin D2 or nicotine.

Aspect 23. The method of aspect 16 wherein generating an aerosol of a cloud of droplets includes generating an aerosol of a cloud of droplets with linalool.

Aspect 24. The method of aspect 16 wherein generating an aerosol of a cloud of droplets includes generating an aerosol of a cloud of droplets with a median droplet size of less than 20 microns.

Aspect 25. The method of aspect 16 wherein generating an aerosol of a cloud of droplets includes generating an aerosol of a cloud of droplets with droplets between 6 microns and 10 microns in size.

Aspect 26. The method of aspect 16 wherein generating an aerosol of a cloud of droplets includes generating an aerosol of a cloud of droplets with at least a majority of the droplets between 5 microns and 10 microns in size.

Aspect 27. The method of aspect 16 wherein generating an aerosol of a cloud of droplets includes generating an aerosol with a mass of the composition as delivered in aerosolized form is less than 1 milligram total mass, and a total quantity of substances acting on TRPV, olfactory, or taste receptors is less than approximately 10 micrograms.

Aspect 28. The method of aspect 16, further comprising: attaching a single or multiple dose disposable cartridge or vial containing the composition to a nutrition cloud generator.

Aspect 29. The method of aspect 16, further comprising: smelling or inhaling the cloud of droplets or ingesting the foodstuff while the cloud of droplets is suspended over a surface of a foodstuff or a beverage, thus bringing the cloud of droplets into an oropharynx of a human.

Aspect 30. The method of aspect 16 wherein providing the aerosol in a space, where the velocity of the generated aerosol cloud is slowed down and reversed such that the cloud becomes relatively quiescent, and from which the aerosol is imbibeable either ortho-nasally or retro-nasally.

Aspect 31. The method of aspect 16 wherein providing the aerosol in a space from which the aerosol is imbibeable either ortho-nasally or retro-nasally includes providing the aerosol directly into an oropharynx of a human.

Aspect 32. The method of aspect 16 wherein providing the aerosol in a space from which the aerosol is imbibeable either ortho-nasally or retro-nasally includes providing the aerosol in a container with an opening from which the cloud can be imbibed.

Aspect 33. The method of aspect 16 wherein providing the aerosol in a space from which the aerosol is imbibeable either ortho-nasally or retro-nasally includes providing the aerosol over a surface of a foodstuff or a beverage.

Aspect 34. The method of aspect 33 wherein a mass of the cloud of droplets dispersed over the foodstuff or beverage is less than 1 milligram total mass, and a total quantity of substances acting on taste, olfactory or TRPV receptors is less than approximately 100 micrograms.

Aspect 35. The method of any of aspects 16 through 34 wherein generating an aerosol of a cloud of droplets includes repeatedly generating the aerosol of the cloud of droplets for defined periods of time, the defined periods of time separated by periods of time during which the generating of the aerosol ceases, to deliver a cumulative therapeutically effective or measured dose over a time that includes two or more of the defined periods of time.

Aspect 36. The method of any of aspects 16 through 34 the composition highlighting cloud created in a range of 12 inches to 1 inch of a nose.

Aspect 37. A method of administering a composition for ortho-nasal or retro-nasal therapeutic applications, method comprising:

during a first period of time, generating a cloud of droplets with agonists or antagonists of at least one type of transient receptor potential vanilloid (TRPV) receptor;

during a second period of time, following the first period of time, stopping the generation of the cloud of droplets; and during a third period of time, following the first and the second periods of time, generating a cloud of droplets with agonists or antagonists of at least one type of TRPV receptor.

Aspect 38. The method of aspect 37, further comprising:

during a fourth period of time, following the first, second and third periods of time, stopping the generation of the cloud of droplets; and during a fifth period of time, following the first, the second, the third, and the fourth of time, generating a cloud of droplets with agonists or antagonists of at least one type of TRPV receptor.

Aspect 39. The method of aspect 37 wherein generating an aerosol of a cloud of droplets includes generating an aerosol of a cloud of droplets where the agonists or antagonists are agonists or antagonists of at least one of TRPV1 receptors, TRPV3 receptors, TRPV4 receptors, or TRPV8 receptors.

Aspect 40. The method of aspect 37 wherein generating an aerosol of a cloud of droplets includes generating an aerosol of a cloud of droplets where the agonists or antagonists are agonists or antagonists of two or more types of TRPV antagonists.

Aspect 41. The method of aspect 37 wherein generating an aerosol of a cloud of droplets includes generating an aerosol of a cloud of droplets with agonists or antagonists of one or both of olfactory receptors or taste receptors.

Aspect 42. The method of aspect 41 wherein the generating a cloud of droplets over a defined number of the periods of time cumulatively produces a cumulative therapeutically effective or measured dose of agonists or antagonists of at least two of three types of receptors, namely TRPV receptors, olfactory receptors, and taste receptors.

Aspect 43. The method of aspect 41 wherein the generating a cloud of droplets over a defined number of the periods of time cumulatively produces a measured dose of agonists or antagonists of three types of receptors, namely TRPV receptors, olfactory receptors, and taste receptors.

Aspect 44. The method of any of aspects 37 through 43 wherein generating a cloud of droplets with agonists or antagonists includes generating the cloud of droplets for up to 10 seconds.

Aspect 45, The method of any of aspects 37 through 43 wherein generating a cloud of droplets with agonists or antagonists includes generating the cloud of droplets for more than 10 seconds and less than 1 minute.

Aspect 46. The method of any of aspects 37 through 43 wherein generating a cloud of droplets with agonists or antagonists includes generating the cloud of droplets for more than 10 minutes.

Aspect 47. The method of any of aspects 37 through 43 wherein generating a cloud of droplets with agonists or antagonists includes generating a cloud of droplets with at least a majority of the droplets between 5 microns and 10 microns in size.

Aspect 48. The method of any of aspects 37 through 43 wherein generating a cloud of droplets with agonists or antagonists includes generating a cloud of droplets with a mass of the agonists or antagonists as is less than 1 milligram total mass, and a total quantity of the agonists or antagonists is less than approximately 10 micrograms.

Aspect 49. The method of any of aspects 37 through 43 wherein generating a cloud of droplets with agonists or antagonists includes generating an aerosol of a cloud of droplets with one or more of the following: sodium iodide, sodium chloride, magnesium chloride, capsaicin, piperine, linalool, ground cinnamon, a cannabinoid, pimento, onion, clove, thyme, ginger, menthol, Irish cream, lemon, lime, mango, raspberry, watermelon, blueberry, strawberry, popcorn, meat, Resolvin D2 or nicotine.

Aspect 50. The method of any of aspects 37 through 43, further comprising:

providing the cloud of droplets with the agonists or antagonists for retro-nasal olfaction.

Aspect 51. The method of any of aspects 37 through 43, further comprising:

targeting a nasal epithelia with the agonists or antagonists.

Aspect 52. A delivery system, the delivery system comprising:

a primary vessel having at least one wall which at least partially delimits an interior of the primary vessel from an exterior thereof, the primary vessel having an outlet port that provides a fluidly communicative path between the interior of the primary vessel and an exterior thereof, the primary vessel further having one or more openings that each provide a respective passage through the at least one wall between the exterior and the interior of the vessel;

a plurality of docks, each dock associated with a respective one of the openings; and at least one distinct delivery device, the at least one distinct delivery device removably dockable to the primary vessel via the at least one the docks thereof, the at least one distinct delivery device comprising a reservoir and an actuator, the reservoir which at least in use holds active substance media, and the actuator controllably operable on the active substance media to cause formation of an aerosol comprising readily-soluble droplets have a median size range of approximately 2 microns to approximately 10 microns and comprising the one or more active substances.

Aspect 53. The delivery system of aspect 52 wherein the at least one distinct delivery device is a nebulizer and further comprises a respective control subsystem communicatively coupled to control the actuator.

Aspect 54. The delivery system of aspect 52 wherein the primary vessel forms a chimney.

Aspect 55. The delivery system of aspect 52 wherein the interior of the primary vessel temporarily retains the aerosol formed by the at least one distinct delivery device when docked thereto and operated to form the aerosol.

Aspect 56. The delivery system of aspect 52 wherein the outlet port of the primary vessel is sized and dimensioned to accommodate a portion of a nose including two nostrils.

Aspect 57. The delivery system of aspect 52 wherein the vessel has a top and the outlet port of the primary vessel is positioned at least proximate the top of the vessel, and the at least one distinct delivery device is positioned relatively below the top of the primary vessel.

Aspect 58. The delivery system of aspect 57 wherein the vessel has a bottom and the at least one distinct delivery device or a portion thereof is oriented to dispense the aerosol toward the bottom of the vessel.

Aspect 59. The delivery system of aspect 57 wherein the vessel has a bottom, an upper surface disposed across above the bottom and disposed across the interior from the bottom to form a chamber, and a neck that extends upwardly from the upper surface, the outlet port at an end of the neck, the docks, the openings located in the upper surface, and wherein the at least one distinct delivery device or a portion thereof is oriented to dispense the aerosol downward at an angle perpendicular to the bottom of the vessel or within 12 degrees of perpendicular.

Aspect 60. The delivery system of aspect 52 wherein the at least one distinct delivery device is a nebulizer that includes a chamber, a mesh screen mounted for oscillation, a microcontroller, and at least one of a piezoelectric transducer, a solenoid, or an electric motor drivingly coupled to oscillate the mesh screen along at least one axis in response to signals from the microcontroller to dispense aerosol into the chamber, the chamber fluidly coupleable to the interior of the primary vessel when the at least one distinct delivery device is coupled to the vessel via one of the docks.

Aspect 61. The delivery system of aspect 60, further comprising:

at least one of a switch or a sensor communicatively coupled to the microcontroller and operable to produce a signal that causes the microcontroller to operate the actuator accordingly.

Aspect 62. The delivery system of aspect 60, further comprising:

at least one of a switch or a sensor communicatively coupled to the microcontroller and operable to produce a signal that causes the microcontroller to operate the actuator in response to the at least one distinct delivery device being coupled to at least one of the docks.

Aspect 63. The delivery system of aspect 60, further comprising:

at least one of a switch or a sensor communicatively coupled to the microcontroller and responsive to a presence or an absence of the vessel with respect to a base and operable to produce a signal that causes the microcontroller to operate the actuator according to the presence or an absence of the vessel with respect to the base.

Aspect 64. The delivery system of aspect 60, further comprising:

at least one of a switch or a sensor communicatively coupled to the microcontroller and responsive to a position or orientation of the vessel and operable to produce a signal that causes the microcontroller to operate the actuator according to the orientation of the vessel.

Aspect 65. The delivery system of any of aspect 61 through 64 wherein the at least one of a switch or a sensor is part of the at least one distinct delivery device.

Aspect 66. The delivery system of aspect 52 wherein the readily-soluble droplets are water droplets.

Aspect 67. The delivery system of aspect 52 wherein the active substance is dissolved in the water droplets.

Aspect 68. The delivery system of aspect 52 wherein the active substance is entrained in the aerosol.

Aspect 69. The delivery system of aspect 52 wherein the active substance is in the form of readily-soluble droplets of the active substance.

Aspect 70. The delivery system of aspect 52 wherein the active substance is encapsulated inside the droplets.

Aspect 71. The delivery device of aspect 52 wherein the at least one distinct delivery device includes a respective a media reservoir holder that in use removably holds at least one media cartridge that contains a therapeutically effective measured dosage of the active substance media.

Aspect 72. A delivery system, the delivery system comprising:

a primary vessel having at least one wall which at least partially delimits an interior of the primary vessel from an exterior thereof, the primary vessel having at least one outlet port that provides a fluidly communicative path between the interior of the primary vessel and an exterior thereof, the primary vessel further having an aperture that each provide a respective passageway through the at least one wall between the exterior and the interior of the vessel;

a dock associated with the aperture; and a distinct delivery device, the distinct delivery device removably dockable to the primary vessel via the dock, the a distinct delivery device comprising a reservoir and an actuator, the reservoir which at least in use holds active substance media, and the actuator controllably operable in response to an orientation of the distinct delivery device to active substance media to cause formation of an aerosol comprising readily-soluble droplets have a median size range of approximately 2 microns to approximately 10 microns and comprising the one or more active substances for imbibing via the at least one outlet port.

Aspect 73. The delivery system of aspect 72 wherein the at least one distinct delivery device is a nebulizer and further comprises a respective control subsystem communicatively coupled to control the actuator.

Aspect 74. The delivery system of aspect 72 wherein the interior of the primary vessel temporarily retains the aerosol formed by the at least one distinct delivery device when docked thereto and operated to form the aerosol.

Aspect 75. The delivery system of aspect 72 wherein the outlet port of the primary vessel is sized and dimensioned to accommodate a portion of a nose including two nostrils.

Aspect 76. The delivery system of aspect 72 wherein the vessel has a top and the outlet port of the primary vessel is positioned at least proximate the top of the vessel, and the at least one distinct delivery device is positioned relatively below the top of the primary vessel.

Aspect 77. The delivery system of aspect 76 wherein the vessel has a bottom and the at least one distinct delivery device or a portion thereof is oriented to dispense the aerosol toward the bottom of the vessel.

Aspect 78. The delivery system of aspect 76 wherein the vessel has a bottom, and wherein the at least one distinct delivery device or a portion thereof is oriented to dispense the aerosol downward at an angle perpendicular to the bottom of the vessel or within 12 degrees of perpendicular.

Aspect 79. The delivery system of aspect 72 wherein the at least one distinct delivery device is a nebulizer that includes a chamber, a mesh screen mounted for oscillation, a microcontroller, and at least one of a piezoelectric transducer, a solenoid, or an electric motor drivingly coupled to oscillate the mesh screen along at least one axis in response to signals from the microcontroller to dispense aerosol into the chamber, the chamber fluidly coupleable to the interior of the primary vessel when the at least one distinct delivery device is coupled to the vessel via one of the docks.

Aspect 80. The delivery system of aspect 72, further comprising:

at least one of a switch or a sensor is responsive to an orientation of at least one of the distinct delivery device or the primary vessel or both, the at least one switch or sensor communicatively coupled to control operation of the actuator.

Aspect 81. The delivery system of aspect 72 wherein the readily-soluble droplets are water droplets.

Aspect 82. The delivery system of aspect 72 wherein the active substance is dissolved in the water droplets.

Aspect 83. The delivery system of aspect 72 wherein the active substance is entrained in the aerosol.

Aspect 84. The delivery system of aspect 72 wherein the active substance is in the form of readily-soluble droplets of the active substance.

Aspect 85. The delivery system of aspect 72 wherein the active substance is encapsulated inside the droplets.

U.S. provisional patent application Ser. No. 62/687,970, filed Jun. 21, 2018; U.S. provisional patent application Ser. No. 62/652,069, filed Apr. 3, 2018; U.S. provisional patent application Ser. No. 62/628,395, filed Feb. 9, 2018; U.S. provisional patent application Ser. No. 62/556,974, filed Sep. 11, 2017; U.S. provisional patent application Ser. No. 62/727,123, filed Sep. 5, 2018; U.S. nonprovisional patent application Ser. No. 16/122,673, filed Sep. 5, 2018 (published as US2019-0105460; and International patent application Ser. No. PCT/US2018/050250 (published as WO 2019/051403), are hereby incorporated by reference, in their entireties. The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A composition for ortho-nasal or retro-nasal food or therapeutic applications, the composition comprising:

an aerosol of droplets dispensed from a nebulizer, the aerosol of droplets having a mass median droplet size of from 3 μm to 20 μm, the droplets of the aerosol of droplets comprising an amount of water or a mixture of water and alcohol and which carry agonists or antagonists of all of: transient receptor potential vanilloid (TRPV) receptors, olfactory receptors, and taste receptors, and wherein a concentration of all agonists or antagonists in the composition is in a range of 50 μg/mL to 2 mg/mL, the composition delivered ortho-nasally and/or retro-nasally as the aerosol of droplets from the nebulizer.

2. The composition of claim 1 wherein the agonists or antagonists of TRPV receptors are agonists or antagonists at least one of TRPV1 receptors, TRPV3 receptors, TRPV4 receptors, or TRPV8 receptors.

3. The composition of claim 1 wherein the composition comprises two or more types of TRPV antagonists.

4. The composition of claim 1 wherein the composition comprises one or more of: ground cinnamon, a cannabinoid, pimento, onion, clove, thyme, ginger, menthol, Irish cream, lemon, lime, mango, raspberry, watermelon, blueberry, strawberry, popcorn, meat, resolvin D2 or nicotine.

5. The composition of claim 1 wherein the droplets of the aerosol of droplets have a mass median droplet size of 5 μm to 10 μm.

6. The composition of claim 1 wherein the droplets of the aerosol of droplets have a mass median droplet size of between 6 μm and 10 μm.

7. The composition of claim 1 wherein a mass of the composition as delivered to a nose as the aerosol of droplets is less than 1 mg total mass, and a total quantity of the agonists or antagonists of TRPV receptors acting on TRPV, olfactory, or taste receptors is less than approximately 100 μg.

8. The composition of claim 1 wherein the concentration of all agonists or antagonists of taste, olfactory and TRPV receptors is in a range of 50 μg/mL to 1 mg/mL.

9. The composition of claim 1 wherein the composition further comprises one or more of: sodium iodide, sodium chloride, and magnesium chloride.

10. The composition of claim 1 wherein the composition further comprises linalool.

11. The composition of claim 10 wherein, at least a majority of the droplets in the aerosol of droplets are between 5 μm and 10 μm in size.

12. The composition of claim 1 wherein the concentration of all agonists or antagonists of TRPV, olfactory, or taste receptors is in a range of 50 μg/mL to 500 μg/mL.

* * * * *